US006261679B1

(12) United States Patent
Chen et al.

(10) Patent No.: US 6,261,679 B1
(45) Date of Patent: Jul. 17, 2001

(54) FIBROUS ABSORBENT MATERIAL AND METHODS OF MAKING THE SAME

(75) Inventors: Fung-jou Chen; Jeffrey Dean Lindsay; Jian Qin; Yong Li, all of Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/083,873

(22) Filed: May 22, 1998

(51) Int. Cl.$^7$ .............................. B32B 5/22; B32B 5/28; B32B 7/12

(52) U.S. Cl. .................. 428/317.9; 425/4 C; 264/45.2; 264/45.3; 427/244; 428/317.1; 428/317.7

(58) Field of Search ................................. 264/45.2, 45.3; 428/317.1, 317.7, 317.9; 427/244

(56) References Cited

U.S. PATENT DOCUMENTS

| 2,423,475 | 7/1947 | Bice et al. | 128/270 |
|---|---|---|---|
| 2,558,395 | 6/1951 | Studer . | |
| 2,597,011 | 5/1952 | MacMasters et al. | 127/32 |
| 2,712,672 | 7/1955 | Calcagno | 18/48 |
| 2,764,159 | 9/1956 | Masci et al. | 128/296 |
| 2,824,092 | 2/1958 | Thompson | 260/117 |
| 3,122,479 | 2/1964 | Smith . | |
| 3,368,911 | 2/1968 | Kuntz et al. | 106/155 |
| 3,471,598 | 10/1969 | Battista | 264/28 |
| 3,474,049 | 10/1969 | Chappelear et al. | 260/2.5 |
| 3,474,050 | 10/1969 | Chappelear et al. | 260/2.5 |
| 3,474,051 | 10/1969 | Chappelear et al. | 260/2.5 |

(List continued on next page.)

FOREIGN PATENT DOCUMENTS

| 2012771 | 11/1990 | (CA) . | |
|---|---|---|---|
| 0 049 944 A1 | 4/1982 | (EP) . | |
| 0 076 888 A2 | 4/1983 | (EP) | 428/317.9 |
| 0 076 888 * | 4/1983 | (EP) | 428/317.9 |
| 0 670 344 A1 | 9/1995 | (EP) . | |
| 900868 | 7/1962 | (GB) . | |
| 3-185197 | 8/1991 | (JP) . | |
| WO 96/02702 A1 | 2/1996 | (WO) . | |
| WO 96/17573 A3 | 6/1996 | (WO) . | |
| WO 96/38232 A1 | 12/1996 | (WO) . | |
| WO 97/32612 A1 | 9/1997 | (WO) . | |
| WO 97/42259 A1 | 11/1997 | (WO) . | |
| WO 99/58091 A1 | 11/1999 | (WO) . | |

OTHER PUBLICATIONS

American Society for Testing Materials (ASTM) Designation: D 3574–86, "Standard Methods of Testing Flexible Cellular Materials—Slab, Bonded, and Molded Urethane Foams," published May 1986.
Hanudelova, Magdalena et al., "Hemostatic Foam," Chemical Abstracts, vol. 81, 1974, p. 343, 68597c.
Koji Hama et al., "Gelatin Sponge For Surgical Treatment," Chemical Abstracts, vol. 47, 1953, 3495g.
Oleneva, G.E. et al., "Production of Porous Starches By Freezing Starch Gels," Chemical Abstracts, vol. 76, p. 83, 1972, 26624a.
Sako, Eiji, "Hemostatic Fillers For Filling the Holes After Extracting Teeth," Chemical Abstracts, vol. 75, 1971, p. 189, 101307j.
"Foamed Plastics," *Kirk–Othmer Encyclopedia of Chemical Technology*, Fourth Edition, vol. 11, John Wiley & Sons Publishers, 1994, pp. 730–783.
"Cellular Materials," *Encyclopedia of Polymer Science and Engineering*, Second Edition, vol. 3, John Wiley and Sons, New York, New York, 1985, pp. 31–40.
Good, Robert J. and Robert R. Stromberg, Editors, *Surface and Colloid Science—vol. II, Experimental Methods*, Plenum Press, New York, 1979, "Techniques of Measuring Contact Angles," pp. 31–91.
Shutov, Dr. Fyodor A., "Cellular Structure and Properties of Foamed Polymers," *Handbook of Polymeric Foams and Foam Technology*, Oxford University Press, New York, 1991, pp. 18–46.
Kuznetsov, A.G. et al., "Use of Surfactants to Improve the Rheological Properties of High–Consistency Wood Fiber Pulp," Derevoobrab. Promst., No. 5, 1995, pp. 2–4, translation attached.
Lachman, Leon and Leonard Chavkin, "A Study of the Lyophilization of Several Pharmaceutical Gums and Suspending Agents," *Journal of the American Pharmaceutical Association*, Scientific Edition, vol. XLVI, No. 7, Jul. 1957, pp. 412–416.
Rinde, J.A., "Preparation and Mechanical Properties of Fiber–Reinforced Foams," *Journal of Cellular Plastics*, Nov./Dec., 1970, pp. 280–287.
Young, Jim, "Lenzing Mill Bringing Second Ozone Bleaching Line Onstream," *Pulp & Paper*, Sep. 1992, pp. 93–95.

Primary Examiner—Richard D. Lovering
(74) Attorney, Agent, or Firm—Gregory E. Croft

(57) ABSTRACT

Disclosed is a fibrous absorbent structure that is wet stable and has large void volume with a density below the critical density of the fiber employed. In one embodiment, the fibrous absorbent uses open-celled foam technologies to keep the fibrous structure expanded and bonded. In other embodiments, the resulting fibrous structure resembles an open-celled polymeric foam, with fibers serving as struts stabilized by binder material. In another embodiment, the resulting fibrous structure is filled with hydrophilic open-celled foams with the cell size substantially smaller than the fibrous pores. Such a wet-stable, high void volume fibrous absorbent can be used in a disposable product intended for the absorption of fluid such as body fluid, including extensible absorbent articles.

87 Claims, 10 Drawing Sheets

U.S. PATENT DOCUMENTS

| | | | |
|---|---|---|---|
| 3,480,569 | 11/1969 | Chappelear et al. | 260/2.5 |
| 3,556,932 | 1/1971 | Coscia et al. | 162/166 |
| 3,556,933 | 1/1971 | Williams et al. | 162/167 |
| 3,562,243 | 2/1971 | Aldrich | 260/111 |
| 3,632,361 | 1/1972 | Battista | 106/122 |
| 3,653,383 | 4/1972 | Wise | 128/296 |
| 3,700,623 | 10/1972 | Keim | 260/80.3 R |
| 3,716,449 | 2/1973 | Gatward et al. | 162/101 |
| 3,767,784 | 10/1973 | Gluck | 424/28 |
| 3,772,076 | 11/1973 | Keim | 117/155 R |
| 3,810,473 | 5/1974 | Cruz, Jr. et al. | 128/334 |
| 3,847,724 * | 11/1974 | Powers et al. | 428/317.7 X |
| 3,867,494 | 2/1975 | Rood et al. | 264/45.3 |
| 3,885,158 | 5/1975 | Flutie et al. | 250/440 |
| 3,899,388 | 8/1975 | Petrovich et al. | 162/164 |
| 3,939,831 | 2/1976 | Cioca et al. | 128/156 |
| 3,992,333 | 11/1976 | Emmons et al. | 260/2.5 R |
| 4,002,173 | 1/1977 | Manning et al. | 128/296 |
| 4,029,100 | 6/1977 | Karami | 128/284 |
| 4,073,840 | 2/1978 | Saidla | 264/45.3 |
| 4,129,528 | 12/1978 | Petrovich et al. | 260/823 |
| 4,147,586 | 4/1979 | Petrovich et al. | 162/135 |
| 4,222,921 | 9/1980 | Van Eenam | 260/29.6 H |
| 4,265,972 | 5/1981 | Rudner | 428/392 |
| 4,292,972 | 10/1981 | Pawelchak et al. | 128/296 |
| 4,372,900 | 2/1983 | Doerfling | 264/45.3 |
| 4,399,085 | 8/1983 | Belbin et al. | 264/41 |
| 4,442,655 | 4/1984 | Stroetmann | 53/428 |
| 4,447,560 | 5/1984 | Piersol | 521/68 |
| 4,474,949 | 10/1984 | Chatterjee et al. | 536/56 |
| 4,522,753 | 6/1985 | Yannas et al. | 260/123.7 |
| 4,535,020 | 8/1985 | Thomas et al. | 428/131 |
| 4,540,625 | 9/1985 | Sherwood | 428/317.7 X |
| 4,543,410 | 9/1985 | Cruz, Jr. | 536/84 |
| 4,554,297 | 11/1985 | Dabi | 521/178 |
| 4,559,243 | 12/1985 | Passler et al. | 427/209 |
| 4,675,394 | 6/1987 | Solarek et al. | 536/43 |
| 4,686,006 | 8/1987 | Cheshire et al. | 162/336 |
| 4,740,528 | 4/1988 | Garvey et al. | 521/128 |
| 4,768,710 | 9/1988 | Sperber | 239/8 |
| 4,806,205 | 2/1989 | Crutchfield et al. | 162/145 |
| 4,868,045 * | 9/1989 | Horiki et al. | 428/317.7 X |
| 4,883,478 * | 11/1989 | Lerailler et al. | 428/317.7 X |
| 4,911,700 | 3/1990 | Makoui et al. | 604/376 |
| 4,969,975 | 11/1990 | Biggs et al. | 264/45.3 X |
| 4,981,557 | 1/1991 | Bjorkquist | 162/168.2 |
| 5,008,344 | 4/1991 | Bjorkquist | 525/328.2 |
| 5,085,736 | 2/1992 | Bjorkquist | 162/168.2 |
| 5,102,738 | 4/1992 | Bell et al. | 428/411.1 |
| 5,104,411 | 4/1992 | Makoui et al. | 8/116.4 |
| 5,128,382 | 7/1992 | Elliott, Jr. et al. | 521/178 |
| 5,131,590 | 7/1992 | Sperber | 239/8 |
| 5,137,551 | 8/1992 | Ahrens et al. | 55/87 |
| 5,147,343 | 3/1998 | Kellenberger | 604/368 |
| 5,147,345 | 9/1992 | Young et al. | 604/378 |
| 5,178,729 | 1/1993 | Janda | 162/101 |
| 5,200,035 | 4/1993 | Bhat et al. | 162/101 |
| 5,266,250 | 11/1993 | Kroyer | 264/45.3 |
| 5,324,561 * | 6/1994 | Rezai et al. | 428/317.9 X |
| 5,328,935 | 7/1994 | Van Phan et al. | 521/64 |
| 5,372,877 | 12/1994 | Kannankeril | 428/283 |
| 5,409,572 | 4/1995 | Kershaw et al. | 162/109 |
| 5,421,922 | 6/1995 | Sperber | 156/71 |
| 5,494,744 | 2/1996 | Everhart et al. | 427/337 |
| 5,506,035 * | 4/1996 | Van Phan et al. | 428/317.9 X |
| 5,506,277 | 4/1996 | Griesbach, III | 521/84.1 |
| 5,507,869 | 4/1996 | Nyberg et al. | 118/308 |
| 5,573,994 | 11/1996 | Kabra et al. | 502/402 |
| 5,612,385 | 3/1997 | Ceaser et al. | 521/68 |
| 5,652,194 | 7/1997 | Dyer et al. | 502/402 |
| 5,707,571 | 1/1998 | Reedy | 264/45.3 |
| 5,738,922 | 4/1998 | Kobayashi et al. | 428/36.5 |
| 5,741,581 | 4/1998 | DesMarais et al. | 428/284 |
| 5,763,067 * | 6/1998 | Brüggeman et al. | 428/317.9 |
| 5,859,076 * | 1/1999 | Kozma et al. | 264/45.2 X |
| 5,948,829 * | 9/1999 | Wallajapet et al. | 521/64 |
| 5,985,434 * | 11/1999 | Qin et al. | 428/315.5 |

\* cited by examiner

FIBROUS ABSORBENT MATERIAL AND METHODS OF MAKING THE SAME

BACKGROUND OF THE INVENTION

In the manufacture of absorbent articles, it is desirable to employ materials having high void volume, a hydrophilic nature, and wet resiliency, or the ability to maintain void volume when wet and when under load. Traditional fluff pulp and creped tissue offer high void volume and are hydrophilic, but they collapse when wetted, especially if a load is applied. Wet laid materials in general suffer from high density due to the largely two-dimensional, planar arrangement of fibers. Air laid materials can have high bulk, but are limited in their stability and resiliency and still have definite limits in porosity and bulk.

Many nonwoven materials made from long synthetic fibers offer high void volume and wet resiliency, but lack inherent hydrophilicity. The fibers can be treated with surfactants or other additives to increase the hydrophilicity of the structure, but such processes are expensive and do not provide the same level of affinity for water offered by cellulose or other hydrophilic polymers. Open cell plastics or plastic foams, also referred to as expanded or sponge plastics, can offer very high void volume and wet resiliency, but suffer the same problem of lacking inherent hydrophilicity and have high cost. Foams made of hydrophilic materials, such as superabsorbent foams, offer the ability to absorb and retain liquids, but can suffer from poor wet resiliency or high cost. Fiber reinforced foams are known wherein fibers are added to increase the strength of a foam matrix, but such materials are generally hydrophobic and lack the high-bulk, absorbent attributes desired of an absorbent article.

Therefore, there is a need for a fibrous structure that has many desirable attributes of a foam, particularly an open-celled foam, but wherein the structure is primarily composed of hydrophilic fibers with fibers serving at least in part as the struts between the open cells.

SUMMARY OF THE INVENTION

It has been discovered that high-bulk fibrous materials suitable for absorbent articles can be made wherein the fibers are oriented in three dimensions. The fibers can be distributed in a substantially uniform distribution or in a substantially nonuniform distribution wherein the fibers serve as struts which define boundaries between three-dimensional void spaces, similar to the solid matrix of an open-cell foam and more particularly similar to the struts in a reticulated open-cell foam. It has also been discovered that known methods and materials for producing foams can be exploited as fiber-structuring tools for the placement, arrangement and binding of hydrophilic fibers, wherein the resulting absorbent fibrous structure has good integrity and resiliency. According to such methods, the fibers are mixed with a structuring composition having a binder material or precursor binding material that can be converted into a water-insoluble binding material, and a removable phase which can be removed from the fibrous mixture to define void spaces. The resulting structure is stabilized by the binder material which serves to hold fibers in place or to establish bonds, particularly water-insoluble bonds, between fibers. In one sense, a preferred embodiment of the invention can be described as a foam-reinforced fibrous network, in contrast to previously known fiber-reinforced foams. In other words, in many embodiments of the present invention, apart from the role played by binder materials in holding fibers together, the components of the structuring composition or foam play a relatively minor structural role in the final absorbent material, once the fibers have been properly positioned and bound.

In another embodiment, the binder material is added to a foamable structuring composition after the fibers have been structured by the foam. Thus, the fibers can be mixed with a structuring composition comprising a removable phase and a non-gaseous phase, and after production of foam, the binder material can be added or, alternatively, a precursor binder material in the structuring composition can be converted to a binder material to provide water-insoluble bonds between fibers in an open, absorbent fibrous structure.

As with traditional open-celled foams, the absorbent fibrous structures of the present invention are generally "open," meaning that the void spaces within the absorbent fibrous structure are substantially interconnected and permit gas transport, analogous to the open nature of open-cell foams. Specifically, an open structure can have at least 50% of the void space in the structure occupied by interconnected voids, and more specifically at least 80% of the void space occupied by interconnected voids. The materials of the present invention are also generally substantially gas permeable, meaning that gas can pass relatively freely through the absorbent fibrous structure in at least one direction, desirably in two orthogonal directions, more desirably in three orthogonal directions, and most specifically in substantially any direction. In one embodiment, the materials of the present invention have a Frazier permeability (hereafter defined) of at least about 50 cfm, more specifically about 100 of more, more specifically still about 200 cfm or more, and most specifically about 400 cfm or more, with an exemplary range of about 75 cfm to about 1100 cfm. In some embodiments, however, the absorbent fibrous structure may have a skin, such as a film of binder material, on one or more surfaces which is liquid or gas impervious, while the interior of the absorbent fibrous structure remains substantially open (apart from any flow restriction caused by the outer skin). For best results in absorbent articles and filters, if a skin exists, at least one portion of the outer surface of the absorbent fibrous structure should be free of either a liquid or gas impervious skin.

Possible uses of the present invention include absorbent articles for intake, distribution, and retention of human body fluids. Examples include feminine care pads, tampons, diapers, incontinence articles, training pants, bed pads, sweat absorbing pads, shoe pads, bandages, helmet liners, wipes and wipers, etc., or, in a suitably thin and flexible form, as a novel tissue or towel. A valuable benefit of many embodiments of the present invention is its ability to maintain a three-dimensional structure and maintain stability under stress and when wet. Thus, a wide variety of shaped composites can be envisioned, including tampons, shock-absorbing shoe pads, articles adapted for particular portions of garments or the body, gaskets for ostomy bags, hemostatic sponges and other medical sponges and absorbents for surgical purposes, dental absorbents such as plugs for extracted teeth or saliva absorbents to fit in portions of the mouth, and the like. Besides serving as absorbent articles, materials of the present invention can serve as components in filters, including filters for absorbing liquid droplets and other entrained materials in the air, including face masks. Filters made with the absorbent fibrous structures of the present invention can be particularly useful when they comprise activated carbon fibers or granules. Such filtration materials are capable of absorbing pollutants or odors from gases and organic pollutants from liquids, particularly water.

The absorbent fibrous structures of the present invention can also be used in additional products such as shock absorbing pads, groundcover materials, erosion barriers, pads for absorbing pet waste, industrial spill and leak absorbents, floating barriers for oil spills and chemical containment, fireproofing materials, insulation, packaging materials, padding, and the like. The absorbent fibrous structures of the present invention can also be combined with other functional materials internally (as by adding material into the absorbent fibrous structure) or externally (as by joining with additional layers) such as odor absorbents, activated carbon materials, fire retardants, superabsorbent particles, nonwoven materials, plastic films or apertured films, extruded webs, closed cell foams, tissue webs, electronic devices such as alarms indicating wetness or leakage, opacifiers, fillers, aerogels, sizing agents, antimicrobial agents, adhesive strips and tapes, and the like.

Hence, in one aspect, the invention resides in a method of producing an open low-density absorbent fibrous structure comprising:
   a) combining hydrophilic fibers with a structuring composition to form a mixture, said structuring composition comprising a binder material and a removable phase;
   b) producing a foam within said mixture;
   c) binding said fibers together with substantially water-insoluble bonds into a continuous, porous network, wherein said binder material stabilizes the porous network.

Said method can further comprise removing a portion of said removable phase, which can be a gas, a liquid, a solid, or a combination thereof. The density of the absorbent fibrous structure suitably can be about 0.2 g/cc (grams per cubic centimeter) or less, particularly about 0.1 g/cc or less, more particularly still about 0.05 g/cc or less, and most particularly about 0.03 g/cc or less, with an exemplary range of from 0.15 g/cc to 0.01 g/cc.

In another aspect, the invention resides in a method of producing a low-density absorbent fibrous structure comprising:
   a) combining hydrophilic fibers with a structuring composition to form a mixture, said structuring composition comprising a binder material and a removable phase;
   b) rearranging said fibers in a three-dimensional structure within said mixture, and desirably into a structure wherein the fibers are substantially oriented in three dimensions;
   c) removing a portion of said removable phase;
   d) binding said fibers together into a continuous, porous network, wherein said binder material forms bonds between said fibers to stabilize said porous network.

In another aspect, the invention resides in a method of preparing an absorbent fibrous composite comprising:
   a) preparing a mixture of hydrophilic fibers with a foamable binder material and an optional carrier liquid, said mixture comprising about 20% or greater hydrophilic fibers on a dry weight basis;
   b) generating a fiber-laden foam from said mixture;
   c) curing said fiber-laden foam to yield an open low-density hydrophilic absorbent fibrous structure.

In yet another aspect, the invention resides in a method of producing a low-density absorbent fibrous structure comprising:
   a) coating hydrophobic fibers with a hydrophilic fiber coating material;
   b) combining said fibers with a structuring composition comprising a binder material and a removable phase to form a mixture;
   c) producing a foam within said mixture;
   d) binding said fibers together into a continuous, porous network, wherein said binder material stabilizes the porous network, and wherein at least about 20%, more specifically at least about 50%, and most specifically at least about 70% of the surface area of said hydrophobic fibers is coated with hydrophilic material.

In another aspect, the invention resides in method of producing a low-density absorbent fibrous structure comprising:
   a) combining hydrophilic fibers with a structuring composition to form a mixture, said structuring composition comprising a non-gaseous phase and a removable phase;
   b) producing a foam within said mixture;
   c) forming water-insoluble bonds with a binder material to bind said fibers together into a continuous, porous structure.

In another aspect, the invention resides in a method of producing a low-density absorbent fibrous structure comprising:
   a) combining hydrophilic fibers with a structuring composition to form a mixture, said structuring composition comprising an optional precursor binder material, a non-gaseous phase and a removable phase, wherein said structuring composition is capable of producing a foam;
   b) removing a portion of said removable phase to form a porous network;
   c) adding binder material to said porous network or converting said precursor binder material to a binder material; and
   d) binding said fibers together into a continuous, porous structure stabilized by said binder material.

In another aspect, the invention resides in a method of producing a low-density absorbent fibrous structure comprising:
   a) combining hydrophilic fibers with a structuring composition to form a mixture, said structuring composition comprising an optional precursor binder material and a removable phase;
   b) rearranging said fibers in a three-dimensional structure within said structuring composition;
   c) removing a portion of said removable phase to form a porous network;
   d) adding binder material to said porous network or converting said precursor binder material to a binder material; and
   e) binding said fibers together into a continuous, porous structure stabilized by said binder material.

In another aspect, the invention resides in a method of producing an open low-density absorbent fibrous structure having at least 25% hydrophilic fibers by dry weight, comprising:
   a) combining hydrophilic fibers with a hydrophilic structuring composition to form a mixture;
   b) applying foam generation means for producing a foam within said mixture;
   c) binding said fibers together with binding means into a continuous, porous network having water-insoluble bonds;
   d) drying said porous network.

In another aspect, the invention resides in an absorbent porous fibrous network made according to any of the above-mentioned methods, as well as absorbent articles made with such a fibrous network, said articles desirably being suited for absorption of human body fluids. For incorporation into absorbent articles known in the art, the absorbent fibrous structures of the present invention can have a thickness less than 3 cm, desirably less than 2 cm, and specifically between about 0.3 cm and 1.7 cm.

In yet another aspect, the invention resides in a foam-structured absorbent fibrous structure comprising a hydrophilic water-insoluble foamable binder material and over 50% by weight of hydrophilic fibers, said fibrous structure having a density of about 0.05 g/cc or less.

In still another aspect, the invention resides in an absorbent fibrous structure comprising a foamable binder material and about 25% or greater by weight of hydrophilic fibers, wherein said fibers are arranged as struts between the cells of an open-cell foam, said fibrous structure being hydrophilic with a density of about 0.1 g/cc or less.

In another aspect, the present invention resides in a layered foam-fiber composite comprising a first fibrous layer and a second fibrous layer, said first layer comprising an absorbent porous fibrous structure comprising a foamable binder material and about 20% or greater by weight of hydrophilic fibers, wherein said fibers are arranged as struts between the cells of an open-cell foam; said second layer comprising a foam-fiber composite having a substantially closed-cell structure or a substantially hydrophobic foam-fiber composite.

In another aspect, the invention resides in an absorbent article comprising a liquid pervious topsheet, a liquid impervious backsheet, and an absorbent fibrous structure disposed between said backsheet and said topsheet, said absorbent fibrous structure comprising at least 25% hydrophilic fibers by weight and more specifically at least 50% hydrophilic fibers by weight, and most specifically at least 70% hydrophilic fibers by weight, and a binder residual from a foamable structuring composition which stabilizes the hydrophilic fibers in a high-bulk structure, said absorbent fibrous structure having a density of about 0.1 g/cc or less and having a Wet Bulk of about 6 cc/g or greater, more specifically about 8 cc/g or greater, more specifically still about 10 cc/g or greater, more specifically still about 15 cc/g or greater, and most specifically about 20 cc/g or greater.

In another aspect, the invention resides in a method for producing a continuous absorbent fibrous structure comprising:

a) combining hydrophilic fibers with a structuring composition comprising a binder material and a removable phase to form a mixture;

b) generating a foam within said mixture;

c) depositing said foam on a moving belt to form a foamed layer without substantial drainage of said structuring composition from said layer;

d) curing said foamed layer to form an absorbent fibrous structure.

In still another aspect, the invention resides in a method for producing a continuous absorbent fibrous structure comprising:

a) forming an air-laid mat of fiberized hydrophilic fibers on a moving belt to form a fibrous mat;

b) impregnating said mat with a foamable structuring composition comprising a binder material and a removable phase;

c) rearranging said fibers in said mat through the action of said structuring composition to create a restructured layer;

d) forming water-insoluble bonds in said restructured layer to form an absorbent fibrous structure.

Said method can further comprise embossing, calendering, perforating, brushing, folding, scoring, perf-embossing, and the like to achieve desired fluid absorbent and mechanical properties.

In another aspect, the invention resides in an apparatus for continuous production of an absorbent fibrous structure, comprising:

a) a mixing unit wherein fibers and a foamable structuring composition comprising a binder material and a removable phase are mixed to form a mixture;

b) a foam generating device capable of producing a fiber-laden foam from said mixture;

c) a moving belt to receive a foamed layer from said foam generating device;

d) a curing unit to create water insoluble bonds in said foamed layer.

In another aspect, the invention resides in an apparatus for continuous production of an expanded fibrous structure, comprising:

a) an air-laying unit for producing a continuous air-laid mat of fluff pulp on a moving belt;

b) an impregnating unit for impregnating said air-laid mat with a foamable structuring composition comprising a binder material and a removable phase;

c) a curing unit to create water insoluble bonds in the impregnated mat, such that an expanded fibrous web is formed.

Based on the theory of foam formation and the role that fibers can play when interacting with a foam, it has been discovered that a hydrophilic fibrous structure can be created in an open cell foam form with the assistance of a structuring composition. For example, using technologies similar to those that produce open-celled foams, it is possible to produce a network of fibers having a three-dimensional fiber orientation and exceptionally high void volume desirably with density well below the critical density at which a fibrous mat or pad will neither collapse nor expand when wetted with water.

Though the structuring composition in some preferred embodiments can be initially an aqueous mixture, the resulting fibrous structure typically lacks the largely two-dimensional, planar fiber arrangement seen in wet-laid structures, for in the present invention there is generally no need for drainage of aqueous components on a foraminous fabric, but the methods of the present invention yield a three-dimensional network structure which, in some embodiments, can resemble a reticulated open-celled foam, wherein the struts between cells consist largely of hydrophilic fibers. Such a structure is capable of high performance as an absorbent material. In many embodiments, therefore, the absorbent fibrous structure is not produced by a wet-laid process requiring drainage of liquid from a fibrous mat.

In contrast to typical fiber-reinforced foams, wherein small quantities of fibers serve to increase the strength of a continuous foam matrix, the structures of preferred embodiments of the present invention can be said to be foam-reinforced fibrous structures or foam-structured fibrous materials, wherein foam technology serves to provide structure and optionally resiliency to a largely fibrous structure. Further, in contrast to typical fiber-reinforced foams, the materials of the present invention can be substantially or predominately hydrophilic.

In contrast to air-laid structures, embodiments of the present invention are structured and given enhanced bulk by the action of a structuring composition comprising non-gaseous components, and can also be prepared by interaction with foamable materials to have properties superior to those of airlaid materials.

Hydrophilic fibers comprise a major portion of the absorbent fibrous structure and can be the predominate structural component of the structure. On a dry mass basis, the percentage of hydrophilic fibers in the absorbent fibrous structure can be about 20% or greater, desirably about 30% or greater, more desirably about 40% or greater, more desirably still about 50% or greater, and most desirably about 55% or greater. Additionally, the hydrophilic fibers can comprise about 80% or greater, or about 90% or greater, or from about 75% to about 98% of the absorbent fibrous structure on a dry mass basis. In many embodiments, the absorbent fibrous structure visually appears to be predominately composed of fibers with relatively little other solid matter visible to the eye. Suitably, the other solid matter is predominantly located at fiber—fiber contact points or both on the surface of the fibers and at fiber—fiber contact points. The fibrous structural elements of the absorbent fibrous structure, consisting of hydrophilic fibers and any relatively thin coating of binder material thereon ("relatively thin" in this context means less than 50% of the fiber diameter), desirably comprise at least about 50% of the solid volume of the absorbent fibrous structure excluding the volume of any loose particulates which may have been added into the structure, and specifically can comprise at least about 60%, more specifically from about 80% to about 98%, most specifically at least about 90%, and alternatively substantially 100% of the solid volume of the absorbent fibrous structure, desirably calculated on a basis which excludes any loose non-fibrous material which may have been added or alternatively excluding the volume of any added superabsorbent material.

The hydrophilic fibers can be any known cellulosic or papermaking fibers, as hereafter defined, such as hardwood or softwood fibers. Hardwood fibers can provide small cells and good strength, such as when the hydrophilic fibers comprise about 30% or more hardwood fibers and more particularly about 50% or more hardwood fibers, while softwood fibers can contribute to higher bulk and good resiliency and stiffness, when desired, such as when the hydrophilic fibers comprise about 30% or more softwood fibers and more particularly about 50% or more softwood fibers. Natural cellulosic fibers such as cotton, kenaf, milkweed, and others can be used, as well as chemically modified or synthetically produced cellulosic fibers. Short hydrophilic textile fibers can also be used, provided the fiber length is suitably short to permit suitable distribution of the fibers by the structuring composition, with average fiber lengths desirably being less than about 15 mm and more desirably less than about 10 mm, with an exemplary range of about 0.5 mm to about 7 mm and more specifically from about 1 mm to about 5 mm. Hydrophilic fibers derived from chitin, chitosan, starch, or other polysaccharides can also be used, though cellulosic fibers generally offer significant benefits due to their abundance, their absorbent nature, and ease of preparation.

While highly fibrillated and highly refined fibers can be used, for certain applications they are undesirable due to excessive flexibility of the fibers, difficulty in drying the fibers, increased energy requirements to fibrillate the fibers, high fines contents, and increased yield losses during fibrillation. Substantially unfibrillated fibers and/or mechanically undamaged fibers are desirable in a variety of embodiments.

In another embodiment, the hydrophilic fibers can be hydrophobic base fibers whose surfaces have been modified to render the fibers substantially hydrophilic. For example, polyethylene, polypropylene, and other synthetic fibers can be rendered substantially or partially hydrophilic through surface modification techniques that involve: 1) irradiating the surface of a polymeric material in the presence of oxygen to create active sites and then chemically grafting a polymer onto the active sites; 2) providing an organic surface coating by plasma discharge in the presence of a plasma polymerizable, halogenated hydrocarbon gas; 3) treating (e.g., oxidizing) the surface of the fibers so that it has a hydrophilic character with a high amount of cation-exchange groups; 4) applying corona discharge treatment, optionally with additional surfactant treatment; 5) depositing surfactants, proteins, polysaccharides or other hydrophilic materials by chemical precipitation, solution coating followed by evaporation of a solvent, supercritical fluid treatment to deposit solubilized hydrophilic agents, and other means known in the art; 6) incorporating water soluble inorganic salts that are hydratable, hygroscopic or —10-deliquescent, deliquescent, onto fiber surfaces, said salts including, for example, toxicologically acceptable calcium and magnesium salts, which can be added to a polymer prior to forming fibers or preferably added to the surfaces of existing fibers. For an example of protein application to hydrophobic materials, see U.S. Pat. No. 5,494,744, issued Feb. 27, 1996 to Everhart et al. For an example of corona discharge treatment, see U.S. Pat. No. 5,102,738, issued Apr. 7, 1992 to Bell et al. With respect to surfactant addition in particular, known methods include (1) passing a formed fibrous web through a bath containing the surfactant in either neat or solution form and drying the wiper as needed so that a given amount of the surfactant is deposited on the wiper, or (2) spraying a surfactant in either neat or solution form on the fibers as they are being formed or on the fibrous porous web and drying the web as needed so that a given amount of the surfactant is deposited on the web, or (3) applying a surfactant in a supercritical carrier fluid such as supercritical carbon dioxide, wherein the carrier fluid desirably causes the fiber to swell during treatment to cause better penetration of the solute into the surface of the fiber, or, (4) adding surfactant to a thermoplastic resin prior to extrusion and formation of the resin into a thermoplastic porous web material. In the later situation, under known process conditions, the added surfactant exudes or migrates to the surface of the fibers of the porous web material during or shortly after fiber formation. This phenomenon has been referred to as "blooming" the surfactant. It is believed that blooming results from the insolubility of the surfactant in the thermoplastic polymer as the polymer cools. See U.S. Pat. No. 4,535,020 to Thomas et al. for an example of surfactant blooming.

In one embodiment, hydrophobic fibers are used in the first step of several methods of the present invention but are coated with a hydrophilic coating material that can be part of the structuring composition or a separate agent. As a separate agent, the hydrophilic coating material can be applied to the fibers before, during, or after the step of combining the fibers with the structuring composition. For example, the fibers may first be treated to render them substantially hydrophilic. In another example, the hydrophobic fibers may be used with the structuring composition to create a three-dimensional nonabsorbent or substantially hydrophobic high-bulk fibrous structure, which is rendered more fully hydrophilic and/or absorbent by the application of a hydrophilic coating material. The coated fibers have hydrophilic matter from the hydrophilic coating material covering a surface area of about 20% or greater, more specifically about 50% or greater, more specifically still about 70% or greater, and most specifically about 90% or greater. The ratio of dry hydrophilic coating material to dry fiber mass can be about 2 or less, more specifically about 0.5 or less, more specifically still about 0.1 or less, more specifically still about 0.05 or less, and most specifically about 0.03 or less.

In another embodiment, the absorbent structure comprises a portion of activated carbon fibers to yield a porous fibrous structure having excellent odor absorbing abilities due to the high permeability of the structure to gas and due to the high fraction of accessible surface area of the fibers. The surface chemistry of the activated carbon fibers should be tailored for optimum absorption or wicking of the target fluids or gases of the fibrous structure and can be rendered hydrophilic. For example, acidic groups on the activated carbon fibers can be desirable for absorbing basic compounds comprising ammonium moieties. Acidic groups can be added by treating the fibers at elevated temperature in the presence of steam, carbon dioxide, nitric acid, and the like. Basic groups, useful for absorbing acidic compounds such as HCl, can be introduced by treatment with ammonia at elevated temperatures or by other treatments known in the art. Suitable fibers and fiber treatment methods include those disclosed in PCT patent application, "Coated Absorbent Fibers," by James Economy and Michael Daley of the University of Illinois, published as WO 96/38232, Dec. 5, 1996, and on the Univ. of Illinois Web site at "http://www.students.uiuc.edu/~ahall/activated carbon fabrics.html" as of January 1998, which discloses a variety of gas treatments at elevated temperature to activate the fibers and control the surface chemistry.

The fibers can additionally contain other additives and agents commonly known in the papermaking arts. Wet strength agents, dry strength agents, crosslinking agents, surface chemistry modifiers, biocides or antimicrobials, softeners, and the like may be present. When recycled fibers or other papermaking fibers are used, a quantity of filler materials such as calcium carbonate or titanium dioxide can be present. For absorbent articles intended to absorb body fluids, it is desirable that post-consumer recycled fibers not be used, though opacifiers, fillers, and other agents can be present or deliberately added. In most cases, virgin papermaking fibers are desirable for their mechanical properties and lack of contaminants. For example, odor-removing additives can be desirably present in the structures of the present invention, including activated carbon granules or fibers, activated silica particulates, EDTA, zeolites, polycarboxylic acids, antibacterial agents, talc powder, sodium bicarbonate, encapsulated perfumes, cyclodextrin, UV absorbers, emollients, chitosan or chitin, and the like.

In the production of such high-bulk absorbent fibrous structures, a structuring composition is used with the fibers. The structuring composition can include certain materials known in the art of foam production and generally serves to hold or rearrange the fibers in a desired three-dimensional orientation. The structuring or rearrangement of fibers can occur by the flow and expansion of a foam; by the expansion of a blowing agent; by the removal of a phase that previously displaced fibers or rearranged them into a foam-like or open-cell structure; by the action of two mixed immiscible phases that act to preferentially position fibers in the liquid meniscus between bubbles; by the hydrodynamic action of a viscous liquid (including solutions) or liquid-solid slurry or frozen slurry which holds the fibers in place during removal of a substantial portion of the liquid or slurry by freeze drying or solvent exchange; and the like.

The physical rearrangement of the fibers can take place in one, two, or three 10 dimensions. Rearrangement in two or more directions is desirable, and rearrangement in three dimensions is most desirable. A one-dimensional rearrangement could occur, for example, when the action of the structuring composition was primarily to move fibers in a mat upward in the z-direction, such that the mat becomes bulkier, but such that the relative x-y positions of the fibers are not substantially changed. Two-dimensional rearrangement occurs when fibers in a narrow layer or plane are moved to new locations in the plane but without crossing or intermingling into other strata. Most desirable is three-dimensional rearrangement, where the action of the structuring composition and more specifically the action of a foam formed by the structuring composition moves fibers not only vertically but also to new x-y locations within a web or mat or other form of the absorbent fibrous structure being made. For example, bulk motion of a fiber-laden froth or foam due to beating, stirring, pouring, molding, and the like can result in a three-dimensional rearrangement of fibers prior to binding of the fibers. In general, physical rearrangement of the fibers in a particular direction or dimension can be said to occur if, for example, a characteristic fiber is typically displaced by about 1 mm or greater, more specifically about 3 mm or greater, more specifically still about 10 mm or greater, and most specifically about 5 mm to about 25 mm.

In one embodiment, the structuring composition is sufficiently viscous and/or stable that it does not separate substantially from the fibers by drainage after mixing over a time space sufficient to dry or cure the structuring composition. (Curing of the structuring composition occurs when the binder material forms bonds which stabilize the fibers, and can be caused by thermal treatment; condensation reactions or other chemical reactions caused by the effects of electron beams, ultraviolet radiation, microwave radiation, and the like; chemical crosslinking; chemical initiation of polymerization; and the like.) For example, the structuring composition can have a bulk viscosity of about 100 centipoise or greater, more specifically about 500 centipoise or greater, and more specifically still about 2000 centipoise or greater, using methods suitable for viscosity measurement of foams. Thus, it is desirable in certain embodiments that much of the mass of the structuring composition is not removed in liquid form or in liquid/solid form, as by drainage. Specifically, it is desirable in certain embodiments, particularly those involving an aqueous-based foam with gas bubbles, that about 50% or less of the initial mass of the structuring composition be removed in non-gaseous form or by drainage, more specifically that about 10% or less of the initial mass of the structuring composition be removed in non-gaseous form or by drainage, and most specifically that substantially none of the structuring composition be removed in liquid form from the mixture of fibers and structuring composition during formation of the absorbent fibrous structure.

The structuring composition comprises a removable phase which provides void space in the product and a binder material, optionally with a liquid carrier phase and optionally with other non-gaseous components such as surfactants, crosslinking agents, softeners, plasticizers, antimicrobial agents, odor controlling materials, etc., to achieve the desired functional characteristics of the absorbent fibrous structure. At least one component of the structuring composition is non-gaseous. The removable phase can be liquid water or any other liquid capable of being removed by evaporation, solvent exchange, critical point drying, supercritical fluid extraction, wicking, and so forth; ice or other sublimable solids; solids that can be melted and removed as liquids or further evaporated; solids that decompose partially or fully to vapors or fumes upon heating to leave void spaces; and the like. Gas bubbles in a foam as the removable phase are an especially preferred embodiment for ease of production and removal. Desirably, the structuring composition is a foamable composition wherein the bubbles of the foam serve to displace or rearrange the fibers into the desired structure. The binder material stabilizes the porous fibrous structure and can increase the strength of fiber—fiber bonds. Desirably, the structuring composition is hydrophilic once dried or cured. In one embodiment, the removable phase is not liquid water or water vapor and more specifically is not liquid water. In another embodiment, the gas bubbles are largely composed of air or other gases besides water vapor and, in a related embodiment, can be formed without the need to heat aqueous materials to the boiling point, though water vapor bubbles can be employed in other embodiments.

In absorbent fibrous structures derived from a foam generated through the production, generation, or introduction of gas bubbles into the fibrous mixture, the liquid or liquid-solid slurry serves as a non-gaseous phase and the removable phase is the gas that forms bubbles. Since the gas is not chemically bonded to the solid matrix, it is removable by diffusion and desirably by bulk flow, even if some of the original gas in the foam is trapped in some bubbles. Obviously, the gas is removable if the foam has a substantially open-cell structure. In the foam-structures useful for the present invention, at least a portion of the original gas in a foam produced from gas bubbles will be removed from the structure. The portion removed should be a substantial fraction of the removable phase, such as about 20% or more, more specifically about 50% or more, still more specifically about 80% or more, and most specifically about 90% on a volumetric basis. Though it may be ideal to have complete removal of the removable phase, inevitable some small fraction may be trapped in dead end pores, occasional closed pores, and the like.

In a foam produced by liquid phase inversion or by polymerization of one liquid phase around bubbles of another at least partly immiscible liquid, the removable phase is generally a liquid which can be evaporated or otherwise dried to remove it at least in part from the remaining matrix. The structuring composition may also be a solid-liquid suspension or slurry or a three-phase mixture.

The binder material in the structuring composition can be a polymeric material such as a soluble polysaccharide (e.g., carboxymethyl cellulose, starch and modified starches) or a protein (e.g., a gelatin), more specifically a polymeric foamable material. A polymeric binder material may be rendered foamable at least in part due to the presence of foaming agents such as a surfactant or tenside, including anionic, nonionic, and cationic surfactants, in the structuring composition. The polymeric binder material desirably is hydrophilic. A hydrophilic polymeric foamable binder material can require addition of a carrier liquid such as water to create a foam, with water being the preferred carrier fluid, though in a few cases a polymeric foamable binder material can be foamed as is, with egg whites being one example. Desirably, the carrier liquid is a solvent to the polymeric component but not to the hydrophilic fiber (a liquid comprising a solute that renders the hydrophilic fibers soluble or partly soluble, such as a concentrated zinc chloride solution with cellulosic fibers as the hydrophobic fibers, would not be preferred in many embodiments). A material is foamable if a partly or substantially stable foam capable of holding papermaking fibers can be produced by mechanical agitation in the presence of air or upon application of other foaming methods mentioned herein and known to those skilled in the art. Pure water is not foamable, for example, whereas egg whites and many aqueous surfactant solutions are.

The binder material may be water swellable or not water swellable. For best results in absorbent articles, the binder material desirably is substantially water insoluble, even when the binder material is water swellable. Preferably, the binder material provides not only good dry stability but also good wet stability and wet resiliency to the absorbent fibrous structure when wetted with liquid water. For applications where wet resiliency is needed to maintain high void volume even under compressive loads, the binder material desirably is not water swellable, is desirably water insoluble, and desirably has a binder wet strength:dry strength ratio (hereafter defined) of about 10% or greater, specifically about 20% or greater, more specifically about 40% or greater, and most specifically about 50% or greater. The same desirable ranges for binder wet strength:dry strength ratio apply to swellable binder materials as well.

Polymers which are suitable for use in certain embodiments of the present invention include any polymer which is initially soluble in a solvent such that the soluble polymer may be formed into a solution by mixing with a liquid solvent, such as water, and then whereby the polymer is treated to cause the polymer to become water-insoluble and optionally water-swellable so that an absorbent foam comprising such water-insoluble polymer exhibits desired absorbency and physical characteristics.

For swellable binder materials, carboxymethylcellulose (CMC) is a useful material capable of binding fibers and absorbing water. Aside from CMC, polymers which are also suitable for use, particularly for freeze drying and other embodiments of the present invention, include a wide variety of anionic, cationic, and nonionic materials. Suitable polymers include polyacrylamides, polyvinyl alcohols, ethylene maleic anhydride copolymer, polyvinylethers, polyacrylic acids, polyvinylpyrrolidones, polyvinylmorpholines, polyamines, polyethyleneimines, polyacrylamides, polyquaternary ammoniums, natural based polysaccharide polymers such as carboxymethyl celluloses, carboxymethyl starches, hydroxypropyl celluloses, algins, alginates, carrageenans, acrylic grafted starches, acrylic grafted celluloses, chitin, and chitosan, and synthetic polypeptides such as polyaspartic acid, polyglutamic acid, polyasparagins, polyglutamines, polylysines, and polyarginines, as well as the salts, copolymers, and mixtures of any of the foregoing polymers. Polyglucan succinate or glutarate, for example, can also be used, particularly when cross-linked to form diester-crosslinks.

Other useful polymeric materials useful as components of the structuring composition and specifically as binder materials include anionic and cationic latexes, wet strength agents, hydrocolloids, pectin, sodium carboxymethylcellulose, thrombin, collagen, amylose derivatives, algin, synthetic gums, and the like. However, for some applications, it is desirable that the binder not be rubbery and thus not be comprised of latex or related rubbery materials. For products for those who are allergic to latex in particular, latex is not a desirable binder. Where rubber-like mechanical properties are desired, such as in some portions of absorbent pads and particularly gasket materials for absorbent articles, latex can be useful as a binder.

In one embodiment of the present invention, it is desired that the polymer used be a polyelectrolyte for high absorbency. In general, a polyelectrolyte is a glassy polymer. As used herein, the term "glassy" polymer is meant to refer to a polymer having a glass transition temperature (Tg) above about 23° C. (about room temperature) at a relative humidity of about 30 percent or less. Examples of glassy polymers include, but are not limited to, sodium polyacrylate, polyacrylic acid, sodium carboxymethyl cellulose, and chitosan salt polymers. Examples of non-glassy polymers and non-polyelectrolytes include, but are not limited to, polyethylene oxide, polyvinyl acetate, and polyvinyl ether polymers.

Hydrophobic thermoplastics and hot melt adhesives can also serve as the binder material, though it is preferred that they be applied primarily are fiber—fiber contact regions rather than across the entire surface of the fiber to prevent reduction in hydrophilicity of the absorbent fibrous structure. The absorbent fibrous structures of the present invention should be substantially hydrophilic and absorbent.

One property of a water-insoluble polymer which is relevant to its effectiveness in providing a desired amount of liquid-absorbing capacity to an absorbent foam is its molecular weight. In general, a water-swellable, water-insoluble polymer with a higher molecular weight will exhibit a higher liquid-absorbing capacity as compared to a water-swellable, water-insoluble polymer with a lower molecular weight.

The water-insoluble polymers useful in the absorbent fibrous structure of the present invention can generally have a wide range of molecular weights. Polymers suitable as components of the structuring composition or as binder materials useful in the present invention will can have a weight average molecular weight greater than about 10,000, particularly if they are to be swellable, and more specifically greater than about 100,000, even more specifically greater than about 200,000, suitably greater than about 500,000, more suitably greater than about 1,000,000, and up to about 20,000,000. Non-swelling polymers useful as components of a binder material desirably have molecular weights less than about 20,000 and specifically less than about 5,000. Methods for determining the molecular weight of a polymer are well-known in the art.

In some embodiments, the binder material comprises a crosslinked polymer. Crosslinking can be achieved by any method known in the art, including those described in more detail hereafter. Crosslinking can be done before or after removal of the removable phase.

The structuring composition will generally have a pH within the range of from about 2 to about 12, more specifically from about 4 to about 9, more specifically from about 4 to about 7.5, and most specifically from about 6 to about 7.5.

The absorbent fibrous structure can be an "expanded fibrous structure" which, in its dry or cured form, has greater macroscopic volume and greater void volume than the initial mixture of fibers and structuring composition. For example, an expanded fibrous structure can be formed when a fibrous slurry is mixed with a structuring composition containing blowing agents which subsequently are activated to expand and add void volume to the fibrous mixture prior to drying or curing. Likewise, a pressurized mixture of a structuring composition and fibers can expand to occupy increased void when the mixture is depressurized as part of a process for forming an absorbent fibrous structure.

The absorbent fibrous structure of the present invention can be substantially biodegradable. The hydrophilic fibers can be substantially biodegradable. Likewise, the dried structuring composition or the dried binder material can comprise at least 50% by weight, and more specifically at least 80% by weight of biodegradable components, or may be essentially 100% biodegradable.

The fibrous structures of the present invention can have exceptionally low density, such as density significantly below the critical density of the specific fiber type used, such as a density of about any of the following or lower, in units of g/cc: 0.2, 0.15, 0.1, 0.07, 0.05, 0.025, 0.02, and 0.01. For example, structures formed with CMC and eucalyptus fibers by freeze-drying yield a stiff, highly resilient material having a density of only 0.02 g/cc, a remarkably low density structure for a fibrous material.

The absorbent fibrous structure can be flexible according to ASTM definitions for the flexibility of plastic foams, as described hereafter.

Layered structures can be produced with materials of the present invention. In particular, a layered foam-fiber composite can be produced comprising a first fibrous layer and a second fibrous layer, said first layer comprising an absorbent fibrous structure comprising a foamable binder material and about 20% or greater by weight of hydrophilic fibers, wherein said fibers are arranged as struts between the cells of an open-cell foam; said second layer comprising a foam-fiber composite having a substantially closed-cell structure or a substantially hydrophobic foam-fiber composite. In one embodiment of the layered foam-fiber composite, the thickness of said first layer can be less than about 5 mm and the thickness of said second layer can be less than about 4 mm. Additional layers may be attached, including polyolefin bonded carded webs, meltblown webs, spunbond webs, or other materials suitable as surge, intake, or distribution layers for feminine care articles, diapers, incontinence products, and the like. Foams comprising activated carbon materials can also be attached as additional layers.

Unlike many known fiber-reinforced foams and other fibrous composites, the materials of the present invention are generally suitable for use in absorbent articles, and particularly for use in absorbent articles for absorbing human body fluids. In several embodiments, the materials of the present invention have suitable wet resiliency that they are not destroyed or dissolved by application of liquid water, saline solutions, urine, menses, runny bowel movement, sweat, blood, saliva, and the like, and can effectively absorb and retain such fluids, desirably maintaining integrity and shape when completely wetted with saline solution over a prolonged period of time such as 1 hour. In several embodiments, the materials of the present invention have suitable conformability, softness, or flexibility to serve as elements in absorbent articles worn next to the body without discomfort or inadequate body fit. Also, in several embodiments, the materials of the present invention are made without the use of materials and methods inappropriate for human health or without undesired contaminants or waste products such as post-consumer waste, old newspapers, and the like. More specifically, the absorbent fibrous structure can consist essentially of materials that are toxicologically acceptable for prolonged contact with human tissue or for use in a sanitary napkin for feminine care . Most specifically, the absorbent fibrous structure can consist essentially of materials that are toxicologically acceptable for use in a tampon, hemostatic sponge, wound dressing or bandage.

In a further embodiment, the absorbent fibrous structure of the present invention can be provided with a high degree of flexibility through the use of an elastomeric binder material such as latex. The absorbent fibrous structure can then be rendered extensible with such elastomeric bonds, particularly if the material has been suitably molded for extensibility or has been foreshortened mechanical compaction, creping, or rush transfer to create a crepe-like or accordion-like structure permitting expansion and extension in the plane. Slits normal to the direction of extension or not aligned with the direction of extension can also provide extension means to the flexible absorbent fibrous structure, particularly with elastomeric bonds. Thus, absorbent articles such as feminine pads or pantiliners can be made extensible and provided with extensible absorbent cores or other absorbent components through the use of elastomeric bonds in the high bulk, flexible absorbent fibrous structure. Other components in the absorbent article can desirably be extensible as well, including the topsheet, the backsheet, and other absorbent layers, using methods known to those skilled in the art. In the case of a sanitary napkin comprising an absorbent fibrous structure, for example, making the absorbent fibrous structure and desirably also the entire sanitary napkin elastically stretchable will reduce the undesirable tendency of the sanitary napkin to gather longitudinally inward (i.e., bunch longitudinally) when forces which tend to stretch the sanitary napkin are removed.

The absorbent fibrous structure can have gradients in material properties extending in the thickness direction or in directions in the plane of the absorbent fibrous structure. Gradients or variations in basis weight and thickness can readily be provided, but other material properties such as fiber composition, pore size, wettability, and the like can have gradients as well. For example, a planar absorbent fibrous structure suitable for use in an absorbent article may have large pores and large open cells near a top surface, with cells that become progressively smaller near the opposing back surface, optionally terminating in a skin on the back surface which can be partially or substantially liquid impervious. Such a structure with a porosity gradient may be suitable for liquid intake on the top surface but can prevent liquid leakage from the back surface. Articles may be provided with gradients in hydrophilicity as well, with more hydrophilic binder material and fibers in one region (e.g., a top surface) than elsewhere (e.g., a back surface). Gradients may extend in the plane, giving, for example, an article with large cells or pores in a central target region but with more closed cells or smaller pores near the side edges of the absorbent fibrous structure to prevent lateral leakage of fluid.

Methods of Making the Absorbent Fibrous Structure

Many processes known in the art for producing foams and open-cell foams in particular can be used to produce the absorbent fibrous structures of the present invention. In general, a structuring composition is used to help position the fibers and create void space, resulting in a high-bulk mixture which can be dried or cured (as by heat or radiation or application of chemical reagents) into an absorbent fibrous structure.

Methods for producing the absorbent fibrous structure of the present invention begin with preparation of fibers and the structuring composition, which are combined to form a fibrous mixture. The fibers may be in a slurry, such as an aqueous slurry, or may initially be in dry form, such as fluff or comminuted fibers or air lad fiber mats. The structuring composition is desirably capable of producing a foam. The components of the structuring composition may be added to the fibers or visa versa in one step or in multiple stages, optionally with at least some ingredient of the structuring composition being added separately to the mixture at various stages. A portion of the structuring composition may have previously been added to the fibers, which can then react or combine with other reagents in the remainder of the structuring composition that is subsequently added. For example, fibers loaded with sodium bicarbonate may react with citric acid in the remainder of the structuring composition to release carbon dioxide to form a foam, and remaining citric acid may in turn promote crosslinking of the fibers upon subsequent heat treatment.

Following the initial combination of the structuring composition or at least some of its components with the fibers, the removable phase in the structuring composition can be generated or augmented, if necessary, such as by activation of blowing agents to create gas bubbles in the mixture or by direct introduction of extraneous gas through injection or mechanical agitation or high-shear mixing and the like to create a froth or foam. The interaction of the removable phase with other phases in the mixture can reposition and displace the fibers to create a high-bulk fibrous structure, optionally with a distinct bimodal pore size distribution characteristic of an open cell foam with porous struts, wherein the pores in the struts correspond to the small pore spaces between neighboring fibers in a strut, in contrast to the larger pores of the cells defined by the struts.

The steps of creating a foam in the mixture and removing at least a portion of the removable phase typically occur sequentially but can occur simultaneously as well. In many cases, the act of removing a portion of the removable phase creates an open structure in the fibrous structure. In other cases, the structure may become open before significant removal of the removable phase occurs. In some open-cell foaming processes, gas bubbles are first produced and then some of the gas escapes and breaks open windows between the cells to create an open cell foam. In foams created by freeze drying, however, the foam structure is created by the removal of the removable phase (typically water or another suitable volatile material). Likewise, the steps preferably producing a mixture of fibers with the structuring composition and creating the foam therein can also be sequential or simultaneous. The foam may be produced after the mixture is created, it may be produced during the mixing operation, or the foam may already have been created in the structuring composition prior to mixing with the fibers.

Foams can be prepared by many means. The expansion process is that of expanding a fluid polymer phase or slurry to a low density cellular state and then "freezing" the polymer structure by curing or through cooling of the liquid polymer. The extrusion process for producing foams uses physical stabilization in a decompression expansion process. This process uses a blowing agent blended into the molten polymer that is extruded under pressure. This solution of polymer and blowing agent is forced out through a die opening on to a moving belt at normal room temperature and pressure. This reduction in pressure causes the blowing agent to vaporize resulting in expansion of the polymer. The polymer is allowed to cool during expansion such that enough structural strength is obtained for the required density and dimensional stability. Freezing of the structure or stabilization of the polymer structure is a result of the polymer phase cooling to a point below its glass transition temperature. Cooling comes mainly from three areas: (1) the vaporization of the blowing agent, (2) gas expansion, and (3) heat loss to the environment.

Other methods of producing cellular materials include leaching out solid or liquid materials that have been dispersed in a polymer, sintering small particles, dispersing small cellular particles in a polymer, dispersing gas (or solid)

in the fluid state and stabilizing this cellular state, or by sintering polymer particles in a structure that contains a gas phase. In any case, the resulting foam or froth structure comprises a removable phase.

Preparation of reticulated open cell foams can include the application of mechanical force to knock out the windows of closed cells to render them open. Such forces can be applied by one or more cycles of compression, by application of a shock wave, or by thermal shock. Polymeric cell walls can also removed or open by hydrolysis (e.g., by treatment with caustic solution), oxidation, and application of elevated temperature or pressure, as will be recognized by those skilled in the art.

The removable phase may be liquid, gas, or solid, though gas is the most commonly used removable phase in commercial foam production. Nevertheless, many liquids including oils, hydrocarbons, and aqueous fluids can be used as well as some solids such as ammonium bicarbonate which decompose to yield gas upon heating. The interaction of the removable phase with the fibers and other components of the structuring composition results in moving, positioning, or structuring the fibers into a high-void volume form.

The structuring composition can comprise compounds for producing a foam generated through the production, generation, or introduction of gas bubbles into the fibrous mixture. The structuring composition can also comprise compounds for producing a foam via liquid phase inversion or by polymerization of one liquid phase around bubbles of another at least partly immiscible liquid or by other techniques known in the art to produce foams and particularly open-cell foams. In general, when the non-gaseous phase is a liquid distinct from said removable phase, the two phases are sufficiently immiscible over at least a finite range of conditions such as temperature, pressure, chemical environment, and concentration to permit establishment of interfacial regions between said phases. The fibers generally are preferentially attracted to one phase or to an interface, where they are largely held in place during removal of at least a part of the removable phase to yield a porous fibrous structure. Binder materials, desirably in a liquid phase of the structuring composition, serve to increase the integrity of the fibrous structure during or after removal of at least part of the removable phase.

A related embodiment, by way of example, can have a solid, semi-solid or gel phase as the removable phase and a liquid phase as a separate non-gaseous phase. It is desirable, however, that the binder material not swell significantly (e.g., the volume increase is less than 400%, more specifically less than 100%, and more specifically still less than 10% upon saturation with water). In another related embodiment, solid particles can be used to confine the fibers to occupy regions between the particle, whereupon the particle can be removed as by salvation, melting or sublimation for ices or frozen hydrates), shrinkage and physical escape from the fibrous structure, collapse of a hollow particle, and the like.

In preparing an absorbent fibrous structure comprising activated carbon fibers, it is desired that the amount of binding agent be as small as possible to prevent occlusion of pores on the activated carbon fibers. The binding agent can be non-wetting with respect to the activated carbon fibers such that it does not extend over the fiber surface but is primarily located at the menisci where fibers join and touch, thus serving to bind the fibers together in the porous state without severely reducing fiber functionality.

In the case of freeze drying, some solvent exchange operations, supercritical fluid extraction, and other variations of the present invention, a single liquid phase or solution can serve as both the non-gaseous phase and the removable phase. For example, a solution of a polysaccharide in water having high viscosity could be used to hold fibers in a relatively random orientation. The fiber slurry formed with the solution could be rapidly or slowly frozen and freeze dried, wherein the structuring composition now as a frozen solid (both non-gaseous and removable) would serve to hold the fibers in place, depositing the polysaccharide on the fibers as the water sublimes, thus increasing the integrity of the fiber network, which may require further cross linking treatment or curing or addition of other binder materials for full strength and resiliency development. Freeze drying technology for foam production is also disclosed in commonly owned copending applications, Ser. No. 08/977,918, "Absorbent Foam," now U.S. Pat. No. 5,948,829 and Ser. No. 08/978,263, "Process for Preparing an Absorbent Foam," filed Nov. 25, 1997 now U.S. Pat. No. 5,948,829, both of which are herein incorporated by reference.

In one embodiment, the process generally comprises forming a solution of a soluble polymer in a solvent, mixing the solution with hydrophilic fibers, freezing the solution at a relatively slow cooling rate to a temperature below the freezing point of the solvent, removing the solvent from the frozen solution, and optionally treating the polymer to form a water-swellable, water-insoluble binder material stabilizing an absorbent fibrous structure.

In another embodiment, the process comprises forming a solution of monomers in a solvent, adding hydrophilic fibers, polymerizing the monomers to form a solution gel of a crosslinked polymer in the solvent, freezing the solution gel at a relatively slow cooling rate to a temperature below the freezing point of the solvent, and removing the solvent from the frozen solution gel. Optionally, the solution gel of the crosslinked polymer could be subjected to additional swelling, by using additional solvent, before freezing the solution gel.

In such freeze-drying embodiments, the soluble polymer or the monomers are typically dissolved in a solvent comprising at least about 30 weight percent water, beneficially about 50 weight percent water, suitably about 75 weight percent water, and more suitably 100 weight percent water. When a co-solvent is employed with the water, other suitable solvents include methanol, ethanol, acetone, isopropyl alcohol, ethylene glycol, glycerol, and other solvents known in the art. However, when a water-soluble polymer is used, the use or presence of such other, non-aqueous solvents may impede the formation of a homogeneous mixture such that the polymer does not effectively dissolve into the solvent to form a solution.

The consistency of the fibers in a solution for freeze-drying can be about 10% or less, more specifically from about 0.3% to 4%, more specifically still from about 0.4% to about 2.5%.

It has also been found that the rate at which the solution is cooled from a temperature above the freezing point of the solvent to a temperature below the freezing point of the solvent is helpful in achieving an absorbent foam that exhibits the desired properties described herein. In a qualitative manner, the cooling rate used should not be so fast that visible cracks or visible non-uniformities begin to form in the freezing solution. As such, there is generally a critical cooling rate that will exist for a particular solution in order to achieve a desired absorbent foam of the present invention. Using a cooling rate that is faster than such a critical cooling rate will generally result in an undesirable absorbent foam that exhibits a relatively non-uniform pore structure and cracked polymer matrix. In contrast, using a cooling rate that is slower than such a critical cooling rate will generally result in a desirable absorbent foam that has a relatively uniform pore structure and the absence of any significant cracks or deformities in the polymer matrix.

The cooling rate to be used for a particular suspension plays an important role in the structure of the resulting absorbent fibrous structure. In one embodiment of the present invention, wherein water is the solvent and the polymer is used in a concentration of between about 0.5 to about 2 weight percent, wherein the weight percent is based on the total weight of the solvent, good results have been obtained with a decrease in temperature less than about 0.4° C. per minute, more specifically less than about 0.3° C. per minute, and most specifically less than about 0.1° C. per minute.

Following freezing and sublimation of the ice, the dried material may need to be further treated to activate the binder material and fully effect the binding step. For example, with CMC and many other binder materials, heat treatment is useful to insolubilize the binder material. With latex as a binder material, heat treatment is not usually needed. With certain wet strength resins and crosslinkers, Kymene being one example, some binding can be achieved without heat treatment, but those skilled in the art will recognized that improved wet strength can typically be achieved by curing the resin at an elevated temperature for a brief period of time. As will be recognized by those skilled in the art, soluble proteins likewise can be denatured and cured into water-insoluble or water resistant bonds by thermal treatment, with or without the addition of other crosslinking agents.

A related method for producing open-celled foams for the present invention is that found in U.S. Pat. No. 4,002,173, issued Jan. 11, 1977 to Manning et al., herein incorporated by reference, which discloses "reticulated sponges" or reticulated porous hydrogels comprising a 3-dimensional network of interconnecting strands of diester-crosslinked polyglucan succinate or glutarate, especially of amylose. The sponges are made by lyophilizing (freeze drying) water-soluble salts of the mono- or half-esters, such as water-soluble salts of amylose succinate or amylose glutarate, under process conditions of the invention in the presence of a reticulating agent which causes a controlled melting of the salt solution as it nears the dry state during the lyophilizing step. The resulting reticulated, porous, open-celled sponge is then crosslinked by heating the sponge under dehydrating conditions to form diester-crosslinks. By properly combining fibers and optional additional binder agents into the solution prior to freeze drying, an absorbent fibrous structure can be made.

The absorbent fibrous structure of the present invention is also believed to be capable of being formed by a process generally comprising forming a solution of a soluble polymer in a solvent, adding hydrophilic fibers and a blowing agent to the solution, activating the blowing agent, removing the solvent from the solution, and optionally treating the polymer to form a water-swellable, water-insoluble polymeric matrix binding fibers together in an absorbent fibrous structure.

One embodiment comprises the method of combining hydrophilic fibers, desirably papermaking fibers such as bleached kraft eucalyptus fibers or softwood BCTMP, with a moist, fluidlike or stirrable foam made from a binder material comprising a polymeric material such as a soluble polysaccharide (e.g., carboxymethyl cellulose) or a protein (e.g., a gelatin), more specifically a polymeric foamable material, and optionally an additional foaming agent. The hydrophilic fibers are combined with the polymeric foamable binder material and a carrier fluid, if required, to form a foaming suspension. Desirably, the hydrophilic polymeric binder material and fiber components are dispersed in a carrier liquid such as water or an organic liquid such as an alcohol.

The mixture can then be foamed by the introduction of air by injection and/or mechanical forces, suitably under high mechanical shear or agitation to create the foam and disperse the fibers effectively while preventing significant flocculation. Alternatively, gas bubbles can be created by chemical reaction or other means through the action of a blowing agent in the polymeric foamable binder material. The carrier liquid, if present, or any other volatile liquid compounds, are then removed by solvent extraction, freeze drying, evaporation, radiofrequency drying, microwave drying, and other methods known in the art, yielding a substantially dry, stable, porous, absorbent fibrous structure.

A variety of technologies are known for creation of stable hydrophilic foam structures. Critical point drying can be used to remove a liquid phase without disrupting the porous structure of the solid component. Freeze drying of foams has long been used to create stable foam-like structures from typically aqueous solutions or suspensions of polymers. The freeze-drying (lyophilization) of aqueous protein and carbohydrate solutions is known among those skilled in the art. A loose, foam-, felt- or fleece-like structure having numerous cavities is obtained, which has the consequence that such a dry preparation has a high absorptive capacity relative to body fluids. Either water or a non-aqueous medium such as t-butyl alcohol can be used. While freeze drying is commonly performed on a liquid or slurry largely devoid of gas, a foam-like structure can first be created followed by freeze drying. For example, the methods described above can be used to create an aqueous or alcohol-based foam, followed by freeze-drying to remove at least part of the removable phase without substantial collapse of the foam structure.

For certain high-value products, however, such as medical sponges, freeze-drying can be an economical and desirable process. However, for commercial production, it is desirable that the removal of a removable phase not be conducted by freeze drying or by any process involving freezing of liquid components. Sublimation drying is likewise generally not preferred for commercial production of low-cost, disposable items because of the long times required, particularly for removal of water. Thus, it can be desirable in the production of absorbent articles that the process be carried out without freeze drying, alternatively without freezing, alternatively without substantial sublimation drying, alternatively at a temperature substantially above the freezing point of the structuring composition or, more specifically, above 0° C. and desirably above 5° C.

In combining papermaking and other fibers with a structuring composition according to the present invention, the fibers can be prepared in an aqueous slurry of either low consistency (less than about 4% consistency), medium consistency (about 4% to about 20% consistency), or high consistency. Medium consistency foam preparation requires high input of mechanical energy in most cases but offers economic and structural advantages when used with blowing agents or pressure relief methods for void volume generation, while low consistency slurries can be used to produce freeze-dried structures without foaming or to produce finer foam cells than is normally possible with medium-consistency foams. The use of non-swelling fibers such as cellulosic fibers that have been chemically crosslinked allows better mixing and dispersion at a given moisture content because more of the moisture is available between the fibers rather than taken up by swelling of the fibers. This also improves the ease of drying.

With foaming prior to drying, it is desirable that the fiber-to-carrier liquid mass ratio be high to reduce the amount of liquid removal required, to save energy costs, and to reduce the potential disrupting effect of capillary forces on the open-celled foam structure during removal of carrier fluid. For example, in one embodiment, the fibers are in a medium consistency aqueous slurry at a consistency of about 4% or higher (based on dry fiber mass relative to slurry mass), specifically about 6% or higher, and more specifically from about 8% to about 20%, as foaming begins.

For most effective foaming of a medium or high consistency slurry of paper fibers, high shear is required to put the slurry into a fluidized rheological state in which the slurry no longer acts like a nearly solid mass (as do many high consistency mixtures under static conditions) but behaves rheologically more like a pure liquid. In this state, addition of air or other gases can result in a foam if appropriate surfactants and preferably foam stabilizers are present. In one embodiment, the injected gas is pressurized such that the dispersed gas bubbles will expand as the pressure is relieved. For example, pressurized air or carbon dioxide at about 2 psig or higher, preferably about 10 psig or higher, can be introduced to a pressurized high-shear mixer which permits continuous extrusion of the fiber slurry out one end or through a batch vessel that is periodically depressurized. As the pressure drops, the discrete gas bubbles in the mixture expand until they approach atmospheric pressure. If the pressurized gas is at twice the atmospheric pressure, the gas bubbles may expand in size by a factor of about 2 as the pressure is relieved to increase the available pore volume. Blowing agents can also be used to create gas bubbles in situ in the fiber slurry over a wide range of consistencies.

For the creation of foams from wood pulp slurries, surfactants can be useful in improving fiber flowability or dispersibility under shear.

High-shear mixers acting on pulp suspensions up to consistencies of about 30%, for example, can be used to introduce large amounts of gas into a fiber slurry to provide structure to the fibrous matter. Soap, detergents, tensides, and the like can be added to increase the amount of froth or modify the void volume or bubble size of the mixture. Likewise, proteins or other foam generating or foam stabilizing additives can be used to enhance the stability of the foam and to help bind fibers together in an open-cell array. Crosslinkers, adhesives such as latexes and starch, and other wet strength additives can be further provided either before, during, or after the high-shear mixing to help stabilize the fibrous structure, though addition of such agents preferably occurs before or during the high-shear mixing phase of the process. Following creation of the fibrous foam or expanded fiber mixture, mild agitation can be desirable to prevent settling of liquid or collapse of the foam. The mixture can be air dried, heated by radiation such as microwaves or infrared radiation, inductively heated, heated by conduction or convection, such as by gentle through drying, or the like to dry the fibrous material and optionally to crosslink the structure or cure or set the adhesives or proteins or other binder materials present in the composition.

In one embodiment, the foam-fiber mixture can be prepared from a medium-consistency aqueous fiber slurry with added surfactants and foam stabilizers in a high-shear fiber mixer known in the art of high-consistency bleaching and mixing, including the high shear T-series of fiber mixers from Sunds Defibrator (Norcross, Ga.) and medium consistency mixers from Ahlstrom and from Kamyr. In one embodiment, a foaming agent such as a surfactant and foam stabilizer are mixed with high-consistency fibers, such that the ratio of fibers to liquid water on a mass basis is about 15% or greater, preferably about 20% or greater, more preferably about 25% or greater, and most preferably about 30% or greater. Gas can be introduced at elevated pressure (e.g., above about 5 psi, preferably above 10 psi, more preferably above about 15 psi, and most preferably above 30 psi) into the mixer to produced aerated, slurries of fiber, liquid, and gas. In such an embodiment, the gas will typically comprising less than about 50% by volume in the high shear mixer and more specifically less than about 40% and more specifically still less than about 30%.

Upon release from the high-shear mixer, the gas bubbles swell and create foam cells surrounded by fibers, if the surface tension properties of the liquid are properly adjusted and if the fibers are sufficiently short and dispersed. The resulting porous, three-dimensional foam-fiber composite can then be dried to completion to create a high-bulk fiber structure.

High-shear mixers are generally not preferred for activated carbon fibers because of the tendency for fibers to break. Instead, blowing agents are desired to create the foam from the slurry of fibers in a carrier fluid, which need not be aqueous. Polyurethane, for example, can be suitable with known blowing agents. The polymeric material serving as the foaming agent can also be the carrier fluid in this case, though an additional solvent as the carrier liquid will reduce the viscosity of the mixture and increase the ability to disperse the fibers in a foam at a high fiber to foaming agent ratio, such that the final porous fibrous material after drying or other extraction of the carrier liquid comprises at least 50% fibers by weight.

The mixture need not be foamed prior to drying but can be freeze dried (lyophilized) to yield a structure composed of fibers held in place in part by the polymeric material which is left behind as the carrier fluid is removed. For freeze-drying operations without a prior foaming step, the mixture should be sufficiently dilute with respect to fibers that significant pore space is left upon removal of the carrier fluid. Desirably, the ratio of fiber to carrier fluid is about 30% or less, preferably about 10% or less, and most preferably about 5% or less. Of course, a stable foam with void spaces and bubbles can be created first and then freeze dried to create a wide distribution of pore shapes and sizes.

When hydrophobic thermoplastics and hot melt adhesives serve as the binder material, it is preferred that they be applied primarily are fiber—fiber contact regions rather than across the entire surface of the fiber. This can be achieved by applying the binder material in a solvent or as a suspension in carrier fluid and a allowing menisci to form at fiber—fiber contact points where the binder material is preferentially deposited as the solvent or carrier fluid evaporates. For example, latex spheres or polyolefin microspheres suspended in a carrier liquid can be applied to a fibrous structure in this manner, and then bonding can occur during drying or during heat treatment. The same process can also be used to preferentially apply hydrophilic binder material to fiber—fiber contact regions. In this process, the binder material can be applied after the fibers have been mixed with a structuring composition, in which case at least part of the binder material is not initially contained in the structuring composition that is first mixed with the fibers, but the additional binder material is mixed with the fibers by virtue of applying it to the fibrous network after the fibers have been structured by a structuring composition comprising at least one non-gaseous phase. Thus, in this embodiment, the step of combining fibers with a structuring composition comprising a binder material takes place in two stages: first mixing fibers with a precursor structuring composition, and then adding all or a portion of the binder material to the structured fibrous network. For example, an viscous foam containing a first compound may be used to structure fibers, whereupon a second compound is applied by mist or vapor or gas to the fibrous structure such that the first and second compounds react to form a stable binder material. Further, a fibrous-foam may be stabilized by spraying a cross-linking agent or applying a gas phase which initiates polymerization of a precursor binder material in the structuring composition. Thus, it is recognized that the step of combining hydrophilic fibers with a structuring composition comprising a binder material may actually occur in two substeps, the first substep being the mixing of fibers with a portion of the structuring composition, and the second substep being the addition of a binder material or components of a binder material or a reaction that produces binder material. The second substep can occur after the fibers have been physically rearranged and structured by said portion of the structuring composition. Thus, the binder material can be present in the structuring composition that initially is mixed with the fibers, or a portion of the binder material can be added later after the fibers have been mixed with a structuring composition or a portion of a structuring composition, or a precursor binder material can be present in the structuring composition which later becomes a binder material upon subsequent reaction or physical or chemical change (though the precursor binder material can still be termed a binder material, for example, if it inherently can serve as a binder upon drying, heat treatment, radiative treatment, reaction with other components present in the structuring composition, and the like), or a precursor binder material can become a binder material upon subsequent reaction with a reagent that is applied later to the mixture of fibers and structuring composition. Two-component epoxy adhesives, for example, with a resin (the binding material precursor) and an polymerizing agent, represent an example of a binder material that can be delivered in two steps. Other resins with separate crosslinking agents or polymerization initiators are also known in the art.

In many embodiments, the step of binding the fibers together comprises curing, polymerizing, or cross-linking the binder material to establish water-insoluble bonds. Thermal, radiative, and chemical treatment can be used to promote crosslinking or bond formation.

The step of binding the fibers together can occur in any order. Normally, it will occur after or during removal of the removable phase, but fiber bonding can begin even during mixing with the structuring composition and in general may occur prior to removal of the removable phase.

The structuring composition and binder material generally needs to be dried, particularly if an aqueous solution or suspension is used to form the structuring composition. Drying can be by any method known in the art, but preferably is non-compressive drying to maintain the high void volume of the structure. A degree of compressive drying, such as by contact with heated drums under tension from a dryer fabric, can be used to reduce the bulk to a desired level, and calendering, embossing, perforating, or pressing may also be performed, if needed, to achieve desired bulk levels, softness, uniformity, or other objectives.

Blowing agents for hydrophilic foam systems and other methods of creating hydrophobic foams are known in the art of superabsorbent foam materials. Foamed, water-swellable, polymeric water absorbent material can be prepared by contacting a polymer capable of having a water-swellable character and containing acid moieties in acid form with a blowing agent capable of neutralizing the acid moieties. Carbonate blowing agents can be added to a monomer solution of the monomers used to form the superabsorbent polymer. Other blowing agents can be adapted to the present invention, including those known for polyolefin foam production, such as organic nitrogen compounds (e.g., azodicarbonamide), sodium bicarbonate and citric acid mixtures, sodium borohydride, and the like.

A foam producing technology for use in the present invention is the High-Internal-Phase-Ratio Emulsions (HIPE) technology disclosed in U.S. Pat. No. 5,652,194, "Process for Making Thin-Wet Absorbent Foam Materials for Aqueous Body Fluids," issued Jul. 29, 1997 to Dyer et al., herein incorporated by reference. As described therein, collapsed polymeric foam materials can be typically prepared by polymerizing a particular type of water-in-oil emulsion. Such an emulsion is formed from a relatively small amount of a polymerizable monomer-containing oil phase and a relatively larger amount of a relatively monomer-free water phase. The relatively monomer-free, discontinuous "internal" water phase thus forms the dispersed droplets surrounded by the continuous monomer-containing oil phase. Subsequent polymerization of the monomers in the continuous oil phase forms the cellular foam structure. The aqueous liquid remaining in the foam structure after polymerization can be removed by pressing, thermal drying and/or vacuum dewatering. Polymeric foams, including foams prepared from water-in-oil emulsions, can be relatively closed-celled or, preferably, relatively open-celled in character.

HIPE-type polymeric foams can be characterized as the structures which result when a relatively monomer-free liquid is dispersed as droplets or "bubbles" in a polymerizable monomer-containing liquid, followed by polymerization of the monomers in the monomer-containing liquid which surrounds the droplets. For the purposes of the present invention, the fibers can be dispersed in the continuous phase with a mixer or other method. Upon polymerization, the fibers will trapped in the foam structure forming a portion of the struts between the cells of the foam. The fibers can help prevent collapse of the foam to maintain high bulk.

The resulting polymerized dispersion can be in the form of a porous solidified structure which is an aggregate of cells, the boundaries or walls of which cells comprise solid polymerized material. The cells themselves contain the relatively monomer-free liquid which, prior to polymerization, had formed the droplets in the liquid dispersion.

The oil phase of these HIPE emulsions comprises from about 67 to about 98% by weight of a monomer component having: (a) from about 5 to about 40% by weight of a substantially water-insoluble, monofunctional glassy monomer; (b) from about 30 to about 80% by weight of a substantially water-insoluble, monofunctional rubbery comonomer; (c) from about 10 to about 40% by weight of a substantially water-insoluble polyfunctional crosslinking agent component. The oil phase further comprises from about 2 to about 33% by weight of an emulsifier component that is soluble in the oil phase and will provide a stable emulsion for polymerization. The water or "internal" phase of these HIPE emulsions comprises an aqueous solution containing from about 0.2 to about 20% by weight of a water-soluble electrolyte. The weight ratio of the water phase to the oil phase in these HIPE emulsions ranges from about 12:1 to about 100:1. The polymerized foam is subsequently dewatered (with or without prior washing/treatment steps) to provide the collapsed foam material.

An important aspect of the process of the present invention is to carry out the emulsion formation and polymerization steps in a manner such that coalescence of the relatively small water droplets formed in the HIPE emulsion is reduced. This leads to a number averaged cell size in the resulting polymeric foam material of about 50 microns or less. This reduction in coalescence can be consistently achieved by the use of certain emulsifier systems, by the use of lower temperatures during polymerization (curing), or both, as described hereafter. Moreover, these thin, collapsed absorbent polymeric foam materials can be consistently manufactured according to the process of the present invention on a potentially commercial scale, and at a potentially reasonable or low cost.

According to the present invention, it is not necessary to collapse the foam-like structure involving paper fibers. Indeed, the randomly oriented fibers can resist collapse and help the high-bulk structure maintain its configuration when wetted, particularly if wet-resilient fibers such as chemically cross-linked fibers (e.g., cross-linked prior to incorporation into a foam-like structure) or high-yield fibers are used.

Another useful foam preparation technique involves thermally induced phase separation (TIPS) of polymer solutions. In this technique, a polymer solution is quenched in order to induce phase separation, either through liquid-liquid phase separation or polymer crystallization.

When the TIPS process results in the formation of a continuous polymer-rich phase, two additional processing steps can lead to a foam. First, the morphology of the phase-separated solution is preserved either through vitrification or crystallization of the polymer. This step preserves the small-scale morphology of the demixed solution. Next, the solvent is removed through freeze-drying or supercritical extraction. The TIPS process is a general method whose primary requirement is polymer solubility. Low-density microcellular foams have been prepared with TIPS using many different polymers, including atactic polystirene, isotactic polystirene, poly(4-methyl-1-pentene), polyacrylonitrile, and water-soluble polymers such as (carboxymethyl)cellulose, poly(acrylic acid) and dextran. Water soluble polymers are especially desirable because of their ability to maintain or enhance the absorbent nature of the absorbent fibrous structure.

Another known method for producing foams includes the use of hollow sphere fillers, such as hollow microspheres or hollow macrospheres, which occupy void spaces between the components of a structural matrix. The shell of the hollow sphere is then broken by mechanical forces such as compression or removed, producing an open cell encompassing the volume previously occupied by the hollow sphere prior to breaking or removal of the shell. Microspheres can be about 10 microns to 1 mm in diameter and typically have a shell thickness 1 to about 5 microns, while macrospheres have diameters greater than about 1 mm. Hollow spheres are generally glass or, desirably, polymeric materials which can be removed at least partially by solvents or by heat degradation. Hollow spheres for foam generation are described by F. A. Shutov in the chapter, "Syntactic Polymer Foams" in *Handbook of Polymeric Foams and Foam Technology,* ed. D. Klempner and K. C. Frisch, Hanser Publ., New York, 1991, pp. 355 to 359.

It is emphasized that many approaches can be used to form a fiber network having the structure of the present invention. The foam-formation techniques could include any known in the art, including the use of agitation or air injection with surfactants and polymeric stabilizers followed by freeze-drying or other drying methods, chemical foaming agents, addition of removable foam-template cells (solids of prescribed size and/or size distribution that can be removed from or shrink within a structure after formation to leave void spaced between the fibrous struts; removal can be by solvent extraction, sublimation, and other techniques known in the art), etc.

The foamed mixture prior to drying and any subsequent curing or heat setting steps can be formed, while still in a moldable shape, into any desired form. For example, it can be used to produce a high-bulk planar material, such as insulation or a slab that can be subsequently cut to the desired size or shape for an absorbent article, or it can be directly molded into a three-dimensional shape suitable for a body-fitting element in an absorbent articles or a section shaped for bowel movement containment or adapted to fit into an article of clothing such as a shoe, a helmet for sporting events, a sweat pad or sweat band, and the like.

For production of continuous webs of absorbent fibrous structure for use, many methods can be used. For example, large high shear mixers could be used to produce foamed mixtures of fibers and structuring composition, which could then be extruded, expanded, coated, scraped, or poured onto a moving mesh or belt to form an embryonic foamed web or foam layer. The foam layer can then be molded or shaped into a desired thickness or contoured structure by contact with a second moving web or moving contour elements which slightly compresses the web. The web may be picked up by the moving contour elements or remain on the original belt or wire, after which it is cured or dried to completion, then cut as needed or converted into rolls, stacks of sheets, or packaged groups of absorbent fibrous structures.

An apparatus for the above-mentioned continuous process may include any known mixer, such as rotary mixers, extrusion devices, twin screw mixers, high shear mixers, stirrers, and the like, to create a mixture of the fibers, either in a slurry or as dry fibers, with a foamable structuring composition comprising a binder material (said binder material can include precursor binder materials which must be polymerized or reacted to be effective as binders). The mixture is structured by foaming action and transported to a movable belt or web, including planar webs and textured webs or moving molding units, where it is deposited on the belt or molding units. Desirably, there is no substantial drainage of said structuring composition from said layer through the moving belt or web. The deposited foamed layer is then dried and given further treatments, if needed, to create water-insoluble bonds, in a curing unit, which may be an oven, a radiation chamber (including infrared, electron beams, ultraviolet light, and the like), a chemical reaction chamber where gaseous or liquid reactants are applied to effect curing, and the like.

In one embodiment, a dry, air-laid web of fiberized or comminuted fluff pulp is first deposited on a moving belt to form a mat. The mat is then impregnated with a structuring composition, either in liquid form, which is subsequently converted to a foam suitable for rearranging the fibers of the mat, or in the form of an already created foam which penetrates into the fibrous mat and further expands or swells or otherwise moves to provide new structure to the fibrous mat. In any case, the addition of the structuring composition by impregnation creates a mixture of fibers and a structuring composition. The structuring composition comprises a binder material which is cured by drying or other treatments (e.g., heat treatment, chemical crosslinking, radiation, etc.) applied to the mixture after the fibers have been physically rearranged by action of the structuring composition. The removable phase in this case is a gas, which may be carbon dioxide, air, water vapor, a nitrogen compound, or other gases known in foam-producing methods. The resulting absorbent fibrous structure is preferably an expanded fibrous structure having higher bulk than the fibrous mat prior to impregnation of the structuring composition.

The apparatus for the above-mentioned method can include any known devices for fiberizing or comminuting fibers, such as a hammermill. Papermaking fibers or other hydrophilic fibers are deposited by air into a fibrous mat onto a moving belt, which may be porous to permit air flow through the belt for improved deposition of a fibrous mat. An impregnating unit then applies a foamable structuring composition to the mat. A headbox for foam or other nozzles, scrapers, etc., may push the structuring composition into the mat or it may be applied by a mister or spray device in the air-laying chamber or unit as fibers are being deposited. The structuring composition desirably expands after contact with the fibers and before curing to restructure the fibers and desirably expand the mat. The restructured fibrous mat then passes into a curing unit, either on the belt onto which the mat was deposited or after being removed from said belt and placed on another moving surface. In the curing unit, water-insoluble bonds are formed from the binder material in the structuring composition to create an open, stable absorbent fibrous structure.

In producing a continuous foamed layer on a moving belt, many operations known in the art of papermaking and nonwovens processing may be used to create desired properties and structures, and can be used to restructure the foam and the fibers into desired forms. For example, there can be a finite velocity difference between the moving belt and the foam as the foam is poured, scraped, blown, extruded, brushed, flung, etc., onto the belt, to cause desired anisotropy in the layer properties, the open cell structure, the fiber orientation, and the like. Also, there can be a non-zero impingement angle between a jet or stream of the foam from a headbox, flow spreader, extruder, overflow weir, and the like, as it discharges onto the moving belt or moving molding device. The embryonic, semi-cured, or cured absorbent fibrous structure can be subjected to differential velocity transfer, wherein it is transferred from one moving belt to another belt or fabric with a finite velocity difference. When the transfer is done with rush, i.e., the second belt or fabric is moving at a lower velocity than the first moving belt, the material is foreshortened and is imparted with increased stretch in the machine direction. Transfer to a faster moving belt can be used to stretch out the embryonic semi-cured, or cured absorbent fibrous structure. The absorbent fibrous structure can also be creped to modify texture, impart stretch, increase flexibility, and the like. The absorbent fibrous structure can also be embossed, scored, and the like, either in its dried or cured state, or before drying and curing is complete.

An absorbent fibrous structure can be made extensible in one or more in-plane directions, and desirably elastically extensible in one or more in-plane directions, by molding the structure to impart a texture or macroscopic structure capable or stretch, such as a sine wave or a pleat-like structure. The use of an elastomeric binder is desirable in creating elastic extensibility in the article. In addition to molding, mechanical processes can further impart extensibility, with exemplary processes including rush transfer, creping, foreshortening or in-plane compaction to create pleating, crepe folds, or accordion-like structures in the plane, or aperturing or slitting to create opening that can elongate when stretched. The absorbent fibrous structure can also be laminated with elastomeric or stretchable materials.

In the production of absorbent articles comprising extensible, stretchable, or elastically extensible absorbent fibrous structures, other components such as the topsheet or backsheet can be made extensible or stretchable by suitable molding (thermal molding or vacuum molding, for example) or by performing a mechanical operation, such as pleating, corrugating, stamping, or ring rolling on the topsheet material to provide folds in the material that are able to open when the topsheet is stretched. Apertures and slits can also provide extensibility when stretched. Lamination with elastomer films, elastic bands or threads, stretchable creped tissue, or other stretchable components. Such processes can be performed on many of the topsheet materials and coversheet materials kown in the art for production of absorbent articles for absorbing body fluids.

A continuous web of an absorbent fibrous structure can be molded, shaped or cut into desired shapes for use in absorbent articles. Cutting of the embryonic, semi-cured, or cured absorbent fibrous structure can be done with hydraulic jets, air knives, dies and stamps, metal blades or saws, lasers, and the like. The absorbent fibrous structure can be laminated, joined to, or coupled with elastomeric films or threads, plastic films including apertured films, nonwoven webs such as spunbond or meltblown layers, airlaid materials, creped or uncreped tissue webs, coform composite material, superabsorbent materials and fibers, biodegradable webs, laminated structures, other foam layers, including open cell and closed cell foams and reticulated open cell webs, textiles such as cotton webs, fluff pulp mats, activated carbon materials, and the like, using methods known for high-speed assembly of absorbent articles.

In the continuous or batch production of absorbent fibrous structures, the structure can be imparted with a nonuniform basis weight or thickness distribution during formation, as by laying down a foamed structure with varying basis weight onto a moving belt, or by depositing the embryonic absorbent fibrous structure onto a molded or textured substrate surface that receives differing amounts during deposition or after a scraping or leveling process has removed excess material above a plane over the molded substrate. Alternatively, a three-dimensional mass or thickness distribution can be achieved later, including after curing or drying, by removal of unwanted material as by cutting or pneumatic removal of selected portions. Thickness can be varied nonuniformly by pressing or embossing against nonuniform surfaces.

Gradients in material properties such as cell size or porosity can be achieved with a variety of methods. In some embodiments, a foaming material under the influence of gravity or other body forces will tend to have large bubbles or pores form on one surface. A skin may also form on a surface when a foamed structure is dried or cured adjacent to a solid surface such as a belt, thus creating a gradient in properties. Two or more foamed layers may be combined into a single stratified layer, as by deposition from a layered headbox or by use of separate flow spreaders or extruders, to yield an absorbent fibrous structure having different porosities and material properties in each layer, such as one stratum containing softwood and another stratum containing hardwood fibers, or one stratum having a more wettable (more hydrophilic) binder material than the other strata, or one stratum comprising swellable materials unlike the other strata. For a single, non-stratified layer of an absorbent fibrous structure, steps taken to dry or cure the structure frequently expose one side or surface to different conditions than other portions of the layer, resulting in potential gradients in properties. For example, activation of blowing agents by heat treatment or exposure to a gaseous reagent can result in a gradient in bubbles when the exposure is primarily directed at an exposed surface of the layer while the other surface of the layer rests on a moving belt or other surface. Pressing a heated surface against an absorbent fibrous structure can also preferentially densify or modify one side of the structure. Piercing, lancing, embossing, brushing, and other mechanical treatments can be done to establish other gradients either in the plane or in a thickness direction by selective application of the extent and depth of treatment.

Crosslinked Polymers as the Binder Material

Crosslinked polymers represent a useful class of binder materials suitable for the present invention. Crosslinking may be performed on water-soluble polymers to render them insoluble, for example, and can be particularly useful in the production of freeze-dried materials and other embodiments of the present invention. Crosslinking of the polymer may generally occur either while the polymer is in solution or after the solvent has been removed from the solution used to prepare the absorbent foam. Such crosslinking of the polymer may generally be achieved by either of two different types of crosslinking agents. Such crosslinking agents will generally be soluble in the solvent being used, such as water.

One type of crosslinking agent is a latent crosslinking agent. Suitable latent crosslinking agents are generally either internal latent crosslinking agents or external latent crosslinking agents. An internal latent crosslinking agent is generally copolymerizable to the monomer or monomers used to prepare the polymer and, thus, generally comprise at least one vinyl group and one functional group or functionality that is capable of reacting with the side groups on the base polymer, such as a carboxyl group (COO—) on a sodium polyacrylate polymer or a carboxylic acid group (—COOH) on a polyacrylic acid polymer. Examples of suitable copolymerizable crosslinking agents include ethylenically unsaturated monomers, such as ethylene glycol vinyl ether and amino propyl vinyl ether.

An external latent crosslinking agent generally crosslinks the polymer itself after, for example, the polymer has been formed from the monomer or monomers used to prepare the polymer and/or the polymer has been mixed with a solvent to form a solution. Latent crosslinking agents generally do not take part in the overall polymerization process but, instead, are reactive to the polymer at a later point in time when a proper crosslinking condition is provided. Suitable post treatment conditions include using heat treatment, such as a temperature above about 60° C., exposure to ultraviolet light, exposure to microwaves, steam or high humidity treatment, high pressure treatment, or treatment with an organic solvent. For heat-treatment in general, best results can require a temperature between about 50° C. to about 250° C., more specifically from about 80° C. to about 250° C., more specifically still from about 100° C. to about 200° C., and most specifically from about 100° C. to about 160° C.

Suitable external latent crosslinking agents are any organic compound having at least two functional groups or functionalities capable of reacting with the carboxyl, carboxylic acid, amino, or hydroxyl groups of a polymer. It is desired that such an organic crosslinking agent be selected from the group consisting of diamines, polyamines, diols, and polyols and mixtures thereof; particularly from the group consisting of primary diols, primary polyols, primary diamines and primary polyamines and mixtures thereof. Of the diols and polyols, those possessing longer, such as 4 or greater, carbon chain lengths are generally beneficial. Specifically, the crosslinking agent may be selected from the group consisting of chitosan glutamate, type A gelatin, diethylenetriamine, ethylene glycol, butylene glycol, polyvinyl alcohol, hyaluronic acid, polyethylene imine and their derivatives and mixtures thereof. Other suitable organic crosslinking agents include monochloroacetic acid, sodium chloroacetate, citric acid, butane tetracarboxylic acid, and amino acids such as aspartic acid, and mixtures thereof. Citric acid can be especially desirable in promoting crosslinking and wet resiliency when combined with cellulose and/or cellulose derivatives such as CMC, and then treated at elevated temperature. Another suitable latent crosslinking agent comprises a metal ion with more than two positive charges, such as $Al^{3+}$, $Fe^{3+}$, $Ce^{3+}$, $Ce^{4+}$, $Ti^{4+}$, $Zr^{4+}$, and $Cr^{3+}$. Suitable metal ion crosslinking agents include those of the transition elements which generally have vacant d-orbitals. Suitable metal ion crosslinking agents include $AlCl_3$, $FeCl_3$, $Ce_2(SO_4)_3$, $Zr(NH_4)_4(CO_3)_4$ and $Ce(NH_4)_4(SO_4)_4 \cdot 2H_2O$, other well known metal ion compounds and mixtures thereof. Such metal ion crosslinking agents, when used with a particular polymer, are believed to form ionic bonds with the carboxyl, carboxylic, amino, or hydroxyl groups on the polymer. Metal ions with only two positive charges, such as $Zn^{2+}$, $Ca^{2+}$, or $Mg^{2+}$, are also suitable as crosslinking agents for certain polymers.

When the polymer is a cationic polymer, a suitable crosslinking agent is a polyanionic material such as sodium polyacrylate, carboxymethyl cellulose, or polyphosphate.

A second type of crosslinking mechanism that certain polymers are able to undergo involves a macromolecular rearrangement of the chains of the polymer during the solidification process of the polymer such that the polymer forms a higher ordered structure with a high degree of crystallinity which is generally water insoluble. Polymers suitable to such a crosslinking approach include, but are not limited to, polyvinyl alcohol, chitosan, and carboxymethyl cellulose with a lower degree of carboxymethylation. Additional strong bonding of the polymer could be established between the polymer chains during the solidification process which could result in a generally water insoluble material. An example of this behavior is the strong hydrogen bonding in polyvinyl alcohol forming an insoluble material. A closely related behavior is the formation of hard and soft segments in water soluble polyurethane materials which makes them water swellable but water insoluble.

Suitable crosslinking agents for a polymer solution gel process are also generally of two different types: either internal polymerizable or external crosslinking agent. The first type of crosslinking agent is a polymerizable but instant crosslinking agent. Suitable polymerizable crosslinking agents are generally reactive to the monomer or monomers used to prepare the polymer and, thus, generally comprise at least two functional groups or functionalities that are capable of reacting with the monomers. Examples of suitable polymerizable crosslinking agents include ethylenically unsaturated monomers, such as N,N'-methylene bis-acrylamide for free radical polymerization, and polyamines or polyols for condensation polymerization. The second type of crosslinking agent is a reactive compound having at least two functional groups or functionalities capable of reacting with the carboxyl, carboxylic acid, amino, or hydroxyl groups of a polymer in the solution stage wherein such crosslinking is not latent, in that no additional conditions are needed to initialize the crosslinking reaction. Suitable crosslinking agents may be selected from the group consisting of aldehydes, such as glutaraldehyde, or glycidyl ethers, such as polyethylene gylcol diglycidyl ether.

Another approach to form a crosslinked polymer network in either a polymer solution or on a recovered polymer is the use of a high energy treatment such as electron beam radiation or microwave radiation to form free radicals in the polymer which are then used to generate crosslinking points. This approach is applicable but not limited to instances where a crosslinking agent is not used to prepare the absorbent foam.

If a crosslinking agent is used, it is generally desired that the crosslinking agent be used in an amount that is beneficially from about 0.01 weight percent to about 20 weight percent, more beneficially from about 0.05 weight percent to about 10 weight percent, and suitably from about 0.1 weight percent to about 5 weight percent, based on the total weight of the polymer and the crosslinking agent present in an absorbent foam.

In general, a crosslinking catalyst will not be needed, but may be beneficial, to assist in the crosslinking of the polymer in order to prepare the absorbent foam of the present invention. For example, if citric acid is used as the crosslinking agent, sodium hypophosphite is beneficially used as a crosslinking catalyst. If a crosslinking catalyst is used, it is generally desired that the crosslinking catalyst be used in an amount of from about 0.01 to about 3 weight percent, suitably from about 0.1 to about 1 weight percent, based on the total weight of the polymer used.

Definition of Terms and Test Procedures

"Foams" are two-phase gas-solid systems that have a supporting solid lattice of cell walls that are continuous throughout the structure. The gas (typically air) phase in a foam is usually distributed in void pockets often called cells. "Open-cell foams" are polymeric materials having substantial void space in the form of cells defined by a plurality of mutually connected, three dimensionally branched webs of polymeric material, wherein the cells typically have openings to permit fluid communication from one cell to another. In other words, the individual cells of the foam are for the most part not completely isolated from each other by the polymeric material of the cell walls. Thus the cells in such substantially open-celled foam structures have intercellular openings or "windows" which are large enough to permit ready fluid transfer from one cell to the other within the foam structure. The open-cell foams useful in the present invention generally have a reticulated character. The strands of polymeric material which make up the branched webs of the open-cell foam structure can be referred to as "struts." Sponge-like materials with interconnected cells are an example of open-celled foams.

For purposes of the present invention, a foam material is "open-celled" if at least 80% of the cells in the foam structure that are at least 1 micron size are in fluid communication with at least one adjacent cell. Alternatively, a foam material can be considered to be substantially open-celled if it has a measured available pore volume that is at least 80% of the theoretically available pore volume. In the case of HIPE foams, the theoretically available pore volume can be determined by the water-to-oil weight ratio of the HIPE emulsion from which the foam material is formed.

"Frazier permeability" is measured as standard cubic feet per minute of air flow per square foot of material with an air pressure differential of 0.5 inches of water across the sample. The sample should be substantially planar for a Frazier permeability test and should have a basis weight of about 30 gsm. The materials of the present invention can have Frazier permeabilities of about 50 cfm or above, more specifically about 100 cfm or above, still more specifically about 200 cfm or above, and most specifically about 400 cfm or above, with an exemplary range of from about 75 cfm to about 1100 cfm.

As used herein, an absorbent fibrous structure is "open" if the structure has continuously connected void spaces that allow gas to pass through the sample from at least one surface to an opposing surface.

As used herein, an open-cell foam structure or absorbent fibrous structure has "bimodal pores" if there are at least two distinct classes of pores, a first class comprising cells with boundaries defined by fibrous struts, and a second class defining the smaller pores between neighboring fibers. In other words, the distribution of fibers in the absorbent fibrous structure is not uniform throughout the space of the material, such that distinct cells having no or relatively few fibers can be defined in distinction to the pore spaces between neighboring or touching fibers. Thus, the fibers are preferentially distributed along what may be termed the walls or windows of apparent former bubbles. The absorbent fibrous structures of the present invention can have bimodal pores and heterogeneous distribution of fibers, though certain embodiments, such as those produce by freeze drying, can show relatively high degrees of spatial uniformity in the distribution of the fibers and thus lack a bimodal pore distribution as defined herein. This definition of bimodal pores does not consider the micropores within the fibers themselves.

As used herein, an absorbent fibrous structure is "flexible" if it meets a modified flexibility test based on the flexibility tests for various foams provided by the American Society for Testing and Materials (ASTM). Specifically, a flexible foam is one that does not rupture when a 20×2.5×2.5 cm piece is wrapped around a 2.5 cm mandrel at a uniform rate of 1 lap/5 seconds at 20 degrees Centigrade. "Rigid" foams are those which rupture in the above-mentioned test. Absorbent fibrous structures of the present invention can be either flexible or rigid, with flexible foams being desirable for some body fit applications in certain absorbent articles.

As used herein, "wet flexibility" is determined by a modified form of the foam flexibility test procedure given in the ASTM D 3574-86, 3.3 test used to determine flexibility of cellular organic polymeric foam products. Such a modified test utilizes an absorbent fibrous structure sample which is 7×0.8.×0.8 cm and which has been saturated to its free absorbent capacity with commercially available a saline solution such as SIP certified blood bank saline (Stephens Scientific of Riverdale, N.J., distributed by Baxter Healthcare of McGraw Park, Ill., under catalog #B3158-1) at 37° C. It is important that the cutting process used to make these samples does not introduce edge defects in the strip. The saturated absorbent fibrous structure strip is bent around a 2.5 cm diameter cylindrical mandrel at a uniform rate of 1 lap in 5 seconds. The absorbent fibrous structure is considered flexible if it does not tear or break during this test, i.e., if it passes one bending cycle, then the material is wet flexible.

As used herein, an "expanded fibrous structure" is an absorbent fibrous structure according to the present invention having greater macroscopic volume than the initial mixture of fibers and structuring composition. By virtue of having greater volume, the void volume will also tend to be significantly greater in the expanded fibrous structure than in the initial mixture of the fibers and the structuring composition. The volume of the expanded fibrous structure can be greater than the volume of the initial mixture by about 10% or greater, more specifically by about 100% or greater, more specifically still about 200% or greater, and most specifically by about 50% to about 1000%. By way of illustration, the macroscopic volume can typically be taken as the volume that would be defined by a film shrink-wrapped around the article without compacting the article. For further specificity, if there is any reason for those skilled in the art to be unable to identify the approximate point in time when an "initial mixture" exists in determining whether an absorbent fibrous structure is an expanded fibrous structure, "initial mixture" should then refer to the mixture created within the first 3 seconds of mixing contact between the structuring composition and the hydrophobic fibers.

As used herein, "polymer foams" are materials made by generating void spaces inside a bulk polymer, resulting in substantially reduced density. They can be open-celled or closed-celled. The nature of these cells and the cell size determine many properties of the polymer. For example, light weight and low thermal conductivity are the typical properties of a conventional foam. The density of conventional polystirene foam is in the range of 0.02–0.2 g/cc with closed cells between 50–100 µm in diameter.

As used herein, "critical density" refers to the density at which a fibrous mat or pad will neither collapse nor expand when fully saturated with deionized water at 73° F. For papermaking fibers, the critical density is generally quoted as 0.2 grams/cc but actually ranges from about 0.17 to 0.25 grams/cc, which is generally higher than the typical density of foams. Wet-laid paper sheets tend to have densities near the critical density. The absorbent fibrous structures of the present invention generally are produced at an initial density well below the critical density, such that the critical density is at least 2, 4, 6, 10, 20, or 30 times greater than the dry absorbent fibrous structure density. However, after calendering or other forms of mechanical compression, the density of the absorbent fibrous structure can approach the critical density or be above it, such that the density of the compressed absorbent fibrous structure can be greater than the critical density by a factor of about 1.2 or greater, more specifically 1.5 or greater, and more specifically still about 2 or greater.

"Dry binder material mass fraction" is the oven-dry mass of the structuring composition divided by the combined mass of the oven-dry structuring composition and the dry fibers used to produce an absorbent fibrous structure. In this context, "oven dry" means that the article or material being weighed has been dried at 105° C. for at least 20 minutes such that substantially all of the removal moisture has been driven off. The absorbent fibrous structures of the present invention can have a dry binder material mass fraction of about 0.8 or less, specifically about 0.6 or less, more specifically about 0.5 or less, more specifically still about 0.3 or less, and most specifically about 0.1 or less.

As used herein, "biodegradable" refers to the ability of a compound to ultimately be degraded completely into carbon dioxide and water or biomass by microorganisms and/or natural environmental factors.

As used herein, the term "hydrophobic" refers to a material having a contact angle of water in air of at least 90 degrees. In contrast, as used herein, the term "hvdroDhilic" refers to a material having a contact angle of water in air of less than 90 degrees. For the purposes of this application, contact angle measurements are determined as set forth in Robert J. Good and Robert J. Stromberg, Ed., in "Surface and Colloid Science Experimental Methods," Vol. II, (Plenum Press, 1979), herein incorporated by reference. The absorbent fibrous structures of the present invention are generally hydrophilic as prepared and therefore generally do not require any subsequent treatment to make them hydrophilic. This is in contrast to many absorbent foams known in the art in which the polymeric material of the foam is not inherently hydrophilic.

As used herein, the term "surfactant" includes a single surfactant or a mixture of two or more surfactants. If a mixture of two or more surfactants is employed, the surfactants may be selected from the same or different classes, provided only that the surfactants present in the mixture are compatible with each other. In general, the surfactant can be any surfactant known to those having ordinary skill in the art, including anionic, cationic, and nonionic surfactants. Examples of anionic surfactants include, among others, linear and branched-chain sodium alkylbenzenesulfonates, linear and branched-chain alkyl sulfates, and linear and branched-chain alkyl ethoxy sulfates. Cationic surfactants include, by way of illustration, tallow trimethylammonium chloride. Examples of nonionic surfactants, include, again by way of illustration only, alkyl polyethoxylates; polyethoxylated alkylphenols; fatty acid ethanol amides; and complex polymers of ethylene oxide, propylene oxide, and alcohols.

As used herein, "binder wet strength:dry strength ratio" of a binder material is the ratio of wet tensile strength to dry tensile strength in a fibrous material wherein the fibers are joined solely by the binder material. The wet tensile strength is measured after a sample has been fully wetted with water for 2 minutes and is then divided by the tensile strength of the Tappi conditioned dry sample. A binder that is not attacked, swollen, chemically altered or solubilized by water presumably has a binder wet strength:dry strength ratio of essentially 1.0.

As used herein, "noncompressive drying" refers to drying methods for drying cellulosic webs that do not involve compressive nips or other steps causing significant densification or compression of a portion of the web during the drying process. Such methods include through-air drying; air jet impingement drying; non-contacting drying such as air flotation drying, through-flow or impingement of superheated steam; microwave drying and other radiofrequency or dielectric drying methods; water extraction by supercritical fluids; water extraction by nonaqueous, low surface tension fluids; infrared drying; and other methods.

"Absorbency Under Load" (AUL) is a measure of the liquid retention capacity of a material under a mechanical load. It is determined by a test which measures the amount in grams of an aqueous solution, containing 0.9 weight percent sodium chloride, a gram of a material can absorb in 1 hour under an applied load or restraining force of about 0.3 pound per square inch.

The AUL apparatus comprises a Demand Absorbency Tester (DAT) as described in U.S. Pat. No. 5,147,343, issued Sep. 15, 1992 to Kellenberger, herein incorporated by reference, which is similar to a GATS (Gravimetric Absorbency Test System), available from M/K Systems, Danners, Mass. A level porous plate is used having ports confined within a 2.5 cm. diameter area to provide liquid saline solution, 0.9 (w/w)% NaCl, delivered from a reservoir to the porous plate such that there is no hydraulic head (neither positive pressure nor suction) at the top of the porous plate. Thus, fluid can be absorbed into the absorbent without overcoming a significant capillary pressure barrier to move liquid out of the porous plate. Fluid absorbed from the plate is replaced with liquid from the reservoir, which resides on an electronic balance that measures the amount of liquid removed from the reservoir and absorbed into the absorbent. The sample on the porous plate resides within a section of one-inch (2.54 cm) inside diameter thermoplastic tubing machined-out slightly to be sure of concentricity. 100 mesh stainless steel wire cloth is fused on the bottom of the cylinder to restrain the sample and any particulates therein. Care must be taken to maintain a flat smooth bottom and not distort the inside of the cylinder. A 4.4 g piston is made from one inch diameter solid material (e.g., Plexiglas) and is machined to closely fit without binding in the cylinder. A standard 100 gm weight placed on the piston is used to provide a 21,000 dyne/sq.cm. (about 0.3 psi) restraining load which is commonly experienced in infant diapers. To carry out the test with a foam-like fibrous material or a foam, a material sample is cut into circular discs with a diameter slightly smaller than one inch to freely fit within the sample tube. The sample mass should be from about 0.05 g to about 0.16 g.

This test is initiated by placing a 3 cm diameter GF/A glass filter paper onto the porous plate (the paper is sized to be larger than the inner diameter and smaller than the outer diameter of the cylinder), to insure good contact while eliminating evaporation over the ports of the DAT and then allowing saturation to occur. The material to be tested is placed on the wire cloth at the bottom of the AUL apparatus. The sample is then covered with a plastic spacer disc, weighing 4.4 grams and having a diameter of about 0.995 inch, which serves to protect the sample from being disturbed during the test and also to uniformly apply a load on the entire sample. After carefully placing the piston and weight on the sample in the cylinder, the AUL apparatus is placed on the glass filter paper. The amount of fluid pick-up is monitored as a function of time either directly by hand, with a strip chart recorder or directly into a data acquisition system.

The amount of fluid pickup measured after one hour is the AUL value, expressed as grams of liquid per dry gram of the tested material.

The AUL of the materials of the present invention can be above 6 grams/gram, more specifically about 10 grams/gram or greater, still more specifically about 15 grams/gram or greater, and most specifically about 25 grams/gram or greater, with an exemplary range of from about 9 to about 40 grams/gram. While high AUL values can be achieved without the additional of superabsorbent material or swellable binder material, especially high values of AUL are possible through incorporation of superabsorbent material into the absorbent fibrous structure. Superabsorbent material can be incorporated as loose particulates, particles bound to the hydrophilic fibers, superabsorbent fibers, or as a component of the binder material or structuring composition.

As used herein, "Free Swell Capacity" (FS) is the result of a test which measures the amount in grams of an aqueous solution, containing 0.9 weight percent sodium chloride, that a gram of a material can absorb in 1 hour under negligible applied load. The test is done as described above for the AUL test, except that the 100 gm weight is not placed on the sample.

The Free Swell Capacity of the materials of the present invention can be above 8, more specifically above 10, more specifically above 20, and most specifically above 30 grams/gram.

As used herein, "Free Swell:AUL Ratio" is the ratio of Free Swell Capacity to AUL. It will generally be greater than one. The higher the value, the more sensitive the material is to compressive load, meaning that the sample is less able the sample is to maintain its potential pore volume and capillary suction potential under load. Desirably, the materials of the present invention have "Free Swell:AUL Ratio" of about 4 or less, more specifically about 2 or less, more specifically still about 1.5 or less, and more specifically about 1.3 or less, with an exemplary range of from about 1.2 to about 2.5.

"Cell Pore Size" and "Cell Wall Thickness" are measures of the characteristic size of a cell in a foam (or absorbent fibrous structure) and of the thickness of the wall between adjoining cells, respectively. In making such measurements, a sample is cut by a sharp razor. The cut foam is attached to metal stubs using copper tape and imaged in an environmental scanning electron microscope using 12 kV beam voltage (model E-2020 from Electroscan Corporation of Wilmington, Mass. or a similar instrument). The sample chamber pressure is about 1.2 Torr. The environmental backscatter electron detector is used to collect images, having the advantage of being able to discern any variations in composition. Magnification varies depending on the scale of the subject sample, with a 150 magnification being preferred for a general survey of the sample and a 2500 magnification to measure cell wall thickness and cell size. Cell wall thickness and cell size measurements are taken directly on the environmental scanning electron microscope. Manual measurement of cell wall thickness measurement is used. The cell wall thickness and cell size of each sample are averaged from at least 20 measurements.

"Papermaking fibers," as used herein, include all known cellulosic fibers or fiber mixes comprising cellulosic fibers. Fibers suitable for making the webs of this invention comprise any natural or synthetic cellulosic fibers including, but not limited to: nonwoody fibers, such as cotton, abaca, kenaf, sabai grass, flax, esparto grass, straw, jute hemp, and bagasse, milkweed floss fibers, and pineapple leaf fibers; and woody fibers such as those obtained from deciduous and coniferous trees, including softwood fibers, such as northern and southern softwood kraft fibers; hardwood fibers, such as eucalyptus, maple, birch, aspen, or the like. Woody fibers can be prepared in high-yield or low-yield forms and can be pulped in any known method, include kraft, sulfite, groundwood, TMP, RMP, CTMP, BCTMP, and other known pulping methods. If bleached, any known bleaching method can be used. Synthetic cellulose fiber types include rayon in all its varieties and other fibers derived from viscose or chemically modified cellulose. Chemically treated natural cellulosic fibers can be used such as mercerized pulps, chemically stiffened or crosslinked fibers, sulfonated fibers, and the like. For good mechanical properties in using papermaking fibers, it is often desirable that the fibers be relatively undamaged and largely unrefined or only lightly refined. While recycled fibers can be used, virgin fibers are generally desirable for their mechanical properties and lack of contaminants. Mercerized fibers, regenerated cellulosic fibers, cellulose produced by microbes, rayon, and other cellulosic material or cellulosic derivatives can be used. Suitable papermaking fibers can also include recycled fibers, virgin fibers, or mixes thereof. In certain embodiments capable of high bulk and good compressive properties, the fibers can have a Canadian Standard Freeness of at least 200, more specifically at least 300, more specifically still at least 400, and most specifically at least 500.

As used herein, "high yield pulp fibers" are those papermaking fibers of pulps produced by pulping processes providing a yield of about 65 percent or greater, more specifically about 75 percent or greater, and still more specifically from about 75 to about 95 percent. Yield is the resulting amount of processed fiber expressed as a percentage of the initial wood mass. High yield pulps include bleached chemithermomechanical pulp (BCTMP), chemithermomechanical pulp (CTMP) pressure/pressure thermomechanical pulp (PTMP), thermomechanical pulp (TMP), thermomechanical chemical pulp (TMCP), high yield sulfite pulps, and high yield Kraft pulps, all of which contain fibers having high levels of lignin. Characteristic high-yield fibers can have lignin content by mass of about 1% or greater, more specifically about 3% or greater, and still more specifically from about 2% to about 25%. Likewise, high yield fibers can have a kappa number greater than 20, for example. The preferred high yield pulp fibers, after being prepared by pulping and optional bleaching steps and prior to being formed into dry bales or webs, in one embodiment can also be characterized by being comprised of comparatively whole, relatively undamaged fibers, high freeness (200 Canadian Standard Freeness (CSF) or greater, more specifically 250 CSF or greater, and still more specifically 400 CSF or greater), and low fines content (less than 25 percent, more specifically less than 20 percent, still more specifically less that 15 percent, and still more specifically less than 10 percent by the Britt jar test). In one embodiment, the high-yield fibers are preferably predominately softwood, more preferably northern softwood, and most preferably northern softwood BCTMP.

As used herein, the term "cellulosic" is meant to include any material having cellulose as a major constituent, and specifically comprising at least 50 percent by weight cellulose or a cellulose derivative. Thus, the term includes cotton, typical wood pulps, cellulose acetate, cellulose triacetate, rayon, thermomechanical wood pulp, chemical wood pulp, debonded chemical wood pulp, milkweed, bacterial cellulose, and the like.

"Water retention value" (WRV) is a measure that can be used to characterize some fibers useful for purposes of this invention. WRV is measured by dispersing 0.5 gram of fibers in deionized water, soaking overnight, then centrifuging the fibers in a 1.9 inch diameter tube with a 100 mesh screen at the bottom at 1000 G for 20 minutes. The samples are weighed, then dried at 105° C. for two hours and then weighed again. WRV is (wet weight–dry weight)/dry weight. Fibers useful for purposes of this invention can have a WRV of about 0.7 or greater, more specifically from about 1 to about 2. High yield pulp fibers typically have a WRV of about 1 or greater.

As used herein, "Absorbent Capacity" refers to the amount of distilled water that an initially 1-inch cube of absorbent fibrous material can absorb while in contact with a pool of room-temperature water and still retain after being removed from contact with the pool of liquid water and held on a metal screen and allowed to drip for 30 seconds. Absorbent capacity is expressed as grams of water held per gram of dry fiber. The structures of the present invention have absorbent capacity values of about 5 g/g or greater, preferably about 7 g/g or greater, more preferably from about 8 g/g to about 15 g/g, and most preferably about 9 g/g or greater.

As used herein, "bulk" and "density," unless otherwise specified, are based on oven-dry mass of a sample and a thickness measurement made at a load of 0.05 psi with a three-inch diameter circular platen. Thickness measurements of samples are made in a Tappi conditioned room (50% RH and 73° F.) after conditioning for at least four hours. Samples should be essentially flat and uniform under the area of the contacting platen. Bulk is expressed as volume per mass of fiber in cc/g and density is the inverse, g/cc.

As used herein, "Wet Bulk" is based on a caliper measurement of a sample according to the definition of "bulk" above (at 0.05 psi), except that the conditioned sample is uniformly misted with deionized water until the moistened mass of the sample is approximately 250% of the dry mass of the sample (i.e., the added mass of the moisture is 150% of the dry sample weight). If the sample cannot absorb and retain enough moisture from misting to increase the mass by 150%, then the highest level of achievable moisture add-on below 150% but still above 100% moisture add on should be used. The Wet Bulk is calculated as the thickness of the substantially planar moistened sample under a load of 0.05 psi divided by the oven-dry sample basis weight in g/cc. Absorbent fibrous structures of the present invention can have a Wet Bulk of about 6 cc/g or greater, more specifically about 8 cc/g or greater, more specifically still about 10 cc/g or greater, more specifically still about 15 cc/g or greater, and most specifically about 20 cc/g or greater, with an exemplary range of from about 13 cc/g to about 35 cc/g.

As used herein, a material will be considered to be "water soluble" when it substantially dissolves in excess water to form a solution, thereby losing its initial form and becoming essentially molecularly dispersed throughout the water solution. As a general rule, a water-soluble material will be free from a substantial degree of crosslinking, as crosslinking tends to render a material water insoluble. A material that is "water insoluble" is one that is not water soluble according to the above definition.

As used herein, the term "water-swellable, water-insoluble" is meant to refer to a material that, when exposed to an excess of water, swells to its equilibrium volume but does not dissolve into the water. As such, a water-swellable, water-insoluble material generally retains its original identity or physical structure, but in a highly expanded state, during the absorption of the water and, thus, must have sufficient physical integrity to resist flow and fusion with neighboring materials.

As used herein, the term "solvent" is intended to represent a substance, particularly in a liquid form, that is capable of dissolving a polymer used herein to form a substantially uniformly dispersed mixture at the molecular level. For freeze-drying embodiments, the solvent used in the mixture of fibers and structuring composition needs to be capable of first freezing and then be capable of undergoing sublimation, wherein the solvent passes directly from its frozen state to a vapor state. As such, the solvent should have a freezing point at which the solvent changes from a liquid to a solid.

As used herein, a "portion" of an element represents any non-zero fraction of that element including all of the element. Thus, a portion of the removable phase could be, by way of example, 1%, 5%, 10%, 50%, 90%, or 100% of the removable phase. A portion of a composition having multiple elements could include differing fractions for each element. Thus, by way of example, a portion of a structuring composition comprising surfactant, wet strength resin, starch, and water could be a mixture containing varying amounts of all four ingredients or could be a mixture of just a subset of the ingredients, such as starch, water, and surfactant.

The term "extensible", as used herein refers to articles that can increase in at least one of their dimensions in the x-y plane. The x-y plane is a plane generally parallel to the faces of the article. The term extensible includes articles that are stretchable and elastically stretchable (defined below). In the case of a sanitary napkin comprising an absorbent fibrous structure as an absorbent core or as an intake layer or surge material, for example, the article and the absorbent fibrous structure are desirably extensible both in length and width. The absorbent article, however, may only be extensible in one of these directions. Preferably, the article is extensible at least in the longitudinal direction.

The absorbent article comprising an absorbent fibrous structure or the absorbent fibrous structure can, in addition to being extensible, also be stretchable. The term "stretchable", as used herein, refers to articles that are extensible when stretching forces are applied to the article and offer some resistance to stretching.

An absorbent article comprising the absorbent fibrous structure of the present invention or the absorbent fibrous structure itself also can be elastically stretchable. The terms "elastically stretchable" or "elastically extensible" are intended to be synonymous. These terms, used herein, mean that when in-plane stretching forces are removed, the article or absorbent fibrous structure will tend to return toward its unextended or unstretched dimensions (or original dimensions). It need not return all the way to its unstretched dimensions, however. It may return to relaxed dimensions between its unstretched dimensions and extended (or stretched dimensions).

As used herein, "wet strength agents" are materials used to immobilize the bonds between the fibers in the wet state. Typically the means by which fibers are held together in paper and tissue products involve hydrogen bonds and sometimes combinations of hydrogen bonds and covalent and/or ionic bonds. In the present invention, it is desirable to provide a material that will allow bonding of fibers in such a way as to immobilize the fiber to fiber bond points and make them resistant to disruption in the wet state. In this instance the wet state usually will mean when the product is largely saturated with water or other aqueous solutions, but could also mean significant saturation with body fluids such as urine, blood, mucus, menses, runny bowel movement, lymph and other body exudates.

There are a number of materials commonly used in the paper industry to impart wet strength to paper and board that are applicable to this invention. These materials are known in the art as "wet strength agents" and are commercially available from a wide variety of sources. Any material that when added to a paper web or sheet results in providing the sheet with a wet geometric tensile strength:dry geometric tensile strength ratio in excess of 0.1 will, for purposes of this invention, be termed a wet strength agent. Typically these materials are termed either as permanent wet strength agents or as "temporary" wet strength agents. For the purposes of differentiating permanent from temporary wet strength, permanent will be defined as those resins which, when incorporated into paper or tissue products, will provide a product that retains more than 50% of its original wet strength after exposure to water for a period of at least five minutes. Temporary wet strength agents are those which show less than 50% of their original wet strength after being saturated with water for five minutes. Both classes of material find application in the present invention. The amount of wet strength agent added to the pulp fibers can be at least about 0.1 dry weight percent, more specifically about 0.2 dry weight percent or greater, and still more specifically from about 0.1 to about 3 dry weight percent based on the dry weight of the fibers.

Permanent wet strength agents will provide a more or less long-term wet resilience to the structure. In contrast, the temporary wet strength agents would provide structures that had low density and high resilience, but would not provide a structure that had long-term resistance to exposure to water or body fluids. The mechanism by which the wet strength is generated has little influence on the products of this invention as long as the essential property of generating water-resistant bonding at the fiber/fiber bond points is obtained.

Suitable permanent wet strength agents are typically water soluble, cationic oligomeric or polymeric resins that are capable of either crosslinking with themselves (homocrosslinking) or with the cellulose or other constituent of the wood fiber. The most widely-used materials for this purpose are the class of polymer known as polyamidepolyamine-epichlorohydrin (PAE) type resins. These materials have been described in patents issued to Keim (U.S. Pat. Nos. 3,700,623 and 3,772,076) and are sold by Hercules, Inc., Wilmington, Del., as KYMENE 557H. Related materials are marketed by Henkel Chemical Co., Charlotte, N.C. and Georgia-Pacific Resins, Inc., Atlanta, Ga.

Polyamide-epichlorohydrin resins are also useful as bonding resins in this invention. Materials developed by Monsanto and marketed under the SANTO RES label are base-activated polyamide-epichlorohydrin resins that can be used in the present invention. These materials are described in patents issued to Petrovich (U.S. Pat. No. 3,885,158; U.S. 3,899,388; U.S. 4,129,528 and U.S. 4,147,586) and van Eenam (U.S. Pat. No. 4,222,921). Although they are not as commonly used in consumer products, polyethylenimine resins are also suitable for immobilizing the bond points in the products of this invention. Another class of permanent-type wet strength agents are exemplified by the aminoplast resins obtained by reaction of formaldehyde with melamine or urea.

Suitable temporary wet strength resins include, but are not limited to, those resins that have been developed by American Cyanamid and are marketed under the name PAREZ 631 NC (now available from Cytec Industries, West Paterson, N.J.). This and similar resins are described in U.S. Pat. No. 3,556,932 to Coscia et al. and U.S. Pat. No. 3,556,933 to Williams et al. Other temporary wet strength agents that should find application in this invention include modified starches such as those available from National Starch and marketed as CO-BOND 1000. It is believed that these and related starches are disclosed in U.S. Pat. No. 4,675,394 to Solarek et al. Derivatized dialdehyde starches, such as described in Japanese Kokai Tokkyo Koho JP 03,185,197, may also provide temporary wet strength. It is also expected that other temporary wet strength materials such as those described in U.S. Pat. No. 4,981,557; U.S. 5,008,344 and U.S. 5,085,736 to Bjorkquist would be of use in this invention. With respect to the classes and the types of wet strength resins listed, it should be understood that this listing is simply to provide examples and that this is neither meant to exclude other types of wet strength resins, nor is it meant to limit the scope of this invention.

Although wet strength agents as described above find particular advantage for use in connection with this invention, other types of bonding agents can also be used to provide the necessary wet resiliency. They can be applied at the wet end of the basesheet manufacturing process or applied by spraying or printing, etc. after the basesheet is formed or after it is dried.

DETAILED DESCRIPTION OF THE INVENTION

Figure 1:
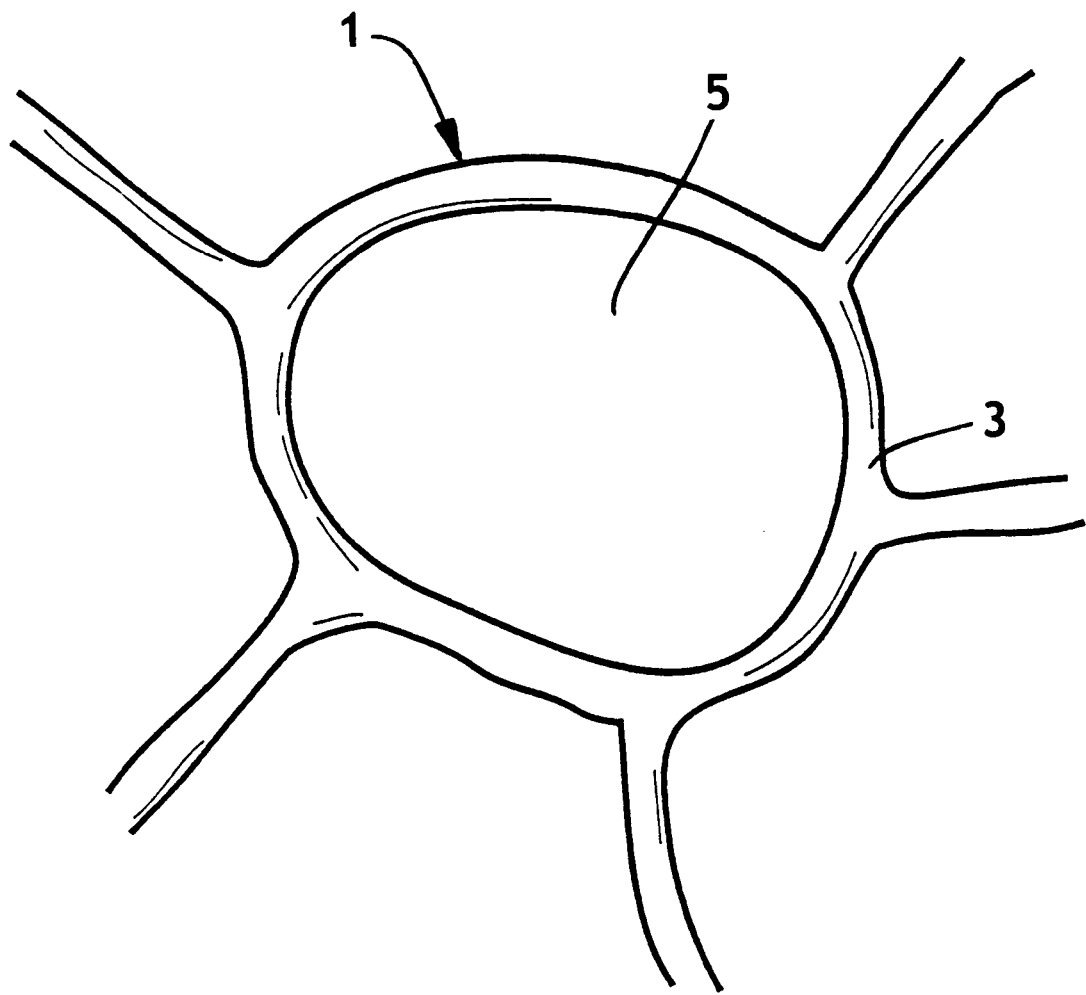
FIG. 1 depicts an element of an open cell foam.

FIG. 1 shows a generic element 1 of an open cell foam having an interconnected solid matrix 3 which surrounds voids 5. Void space 5 may have been part of a bubble face that popped, resulting in an open "window" between the surrounding segments or struts of the matrix 3. Multiple sections such as those shown in FIG. 1 can be arranged in three-dimensional form wherein the solid matrix defines boundaries of interconnected three-dimensional voids.

Figure 2:
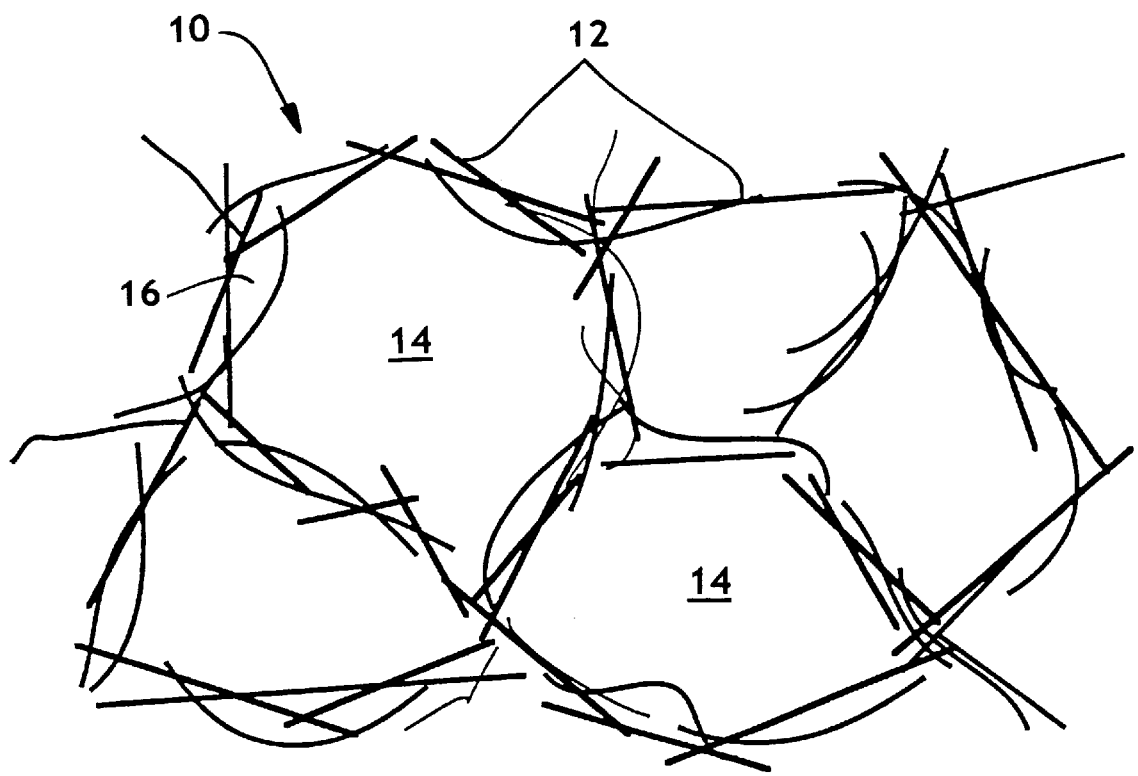
FIG. 2 is a representation of a portion of an absorbent fibrous structure of the present invention having an open-cell foam characteristic.

A portion of an absorbent fibrous structure having a structure resembling an open-celled foam with bimodal pores is shown in FIG. 2. The portion 10 of the absorbent fibrous structure comprises multiple fibers 12 arranged heterogeneously such that open windows 14 are defined between the strut-like arrangements of fibers. The pore space 16 between fibers in a given strut element is substantially smaller than the pore size of the open windows 14 or the three-dimensional cells (not shown) defined by multiple interconnected struts surrounding volumes of space. The absorbent fibrous structures of the present invention can have bimodal pores as shown in FIG. 2 or more homogeneous fiber distributions.

Figure 3:
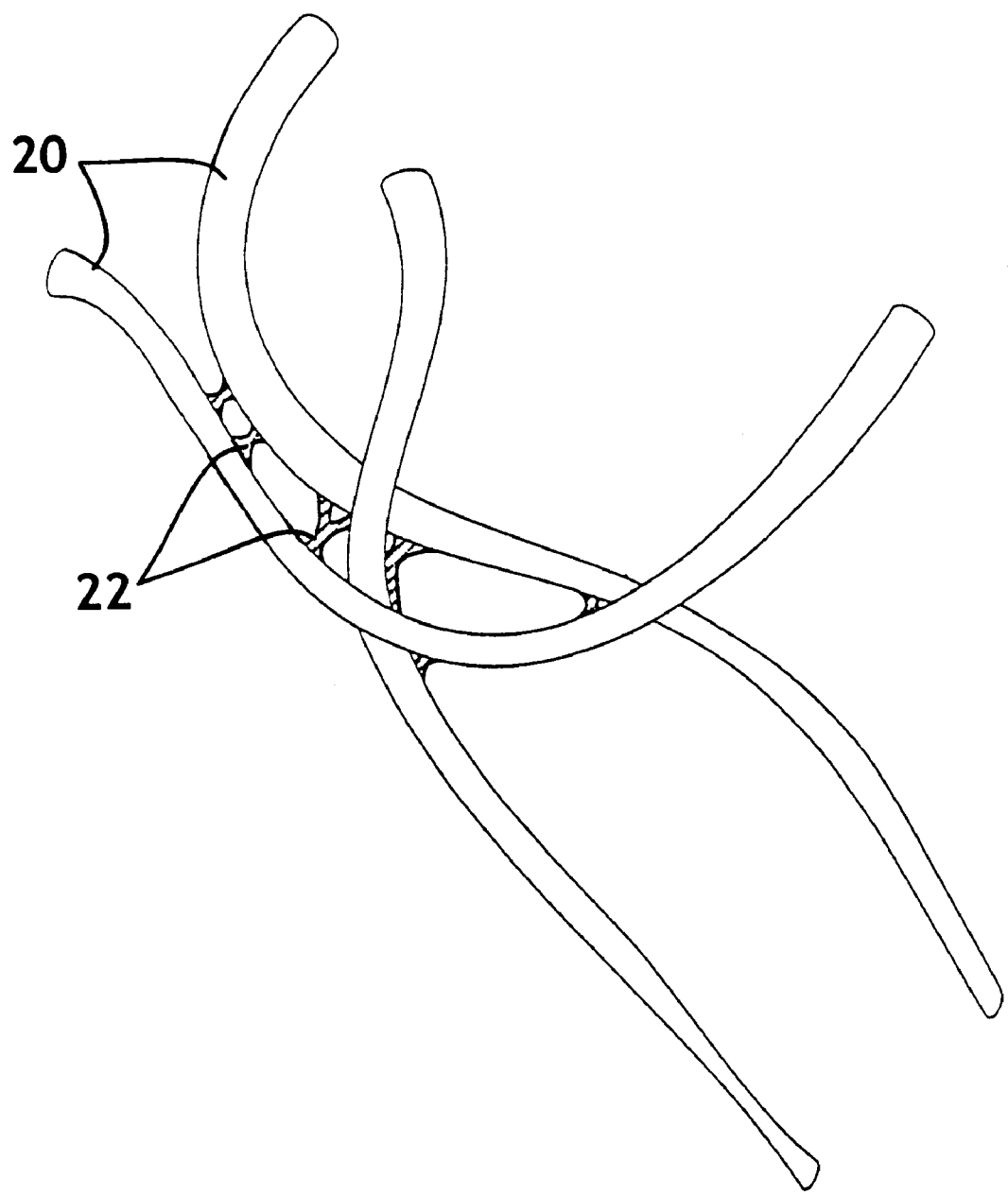
FIG. 3 depicts a adjacent fibers in an absorbent fibrous structure.

FIG. 3 depicts a closer view of adjacent fibers 20 in an absorbent fibrous structure according to the present invention. Fibers 20 are bonded and stabilized in part by the presence of binder material 22, which can be a polymeric material that was present in a foam prior to drying or curing. The foam may be largely collapsed, leaving relatively little structural material in windows and cells between fibers, being primarily concentrated in the smaller spaces between fibers.

Figure 4:
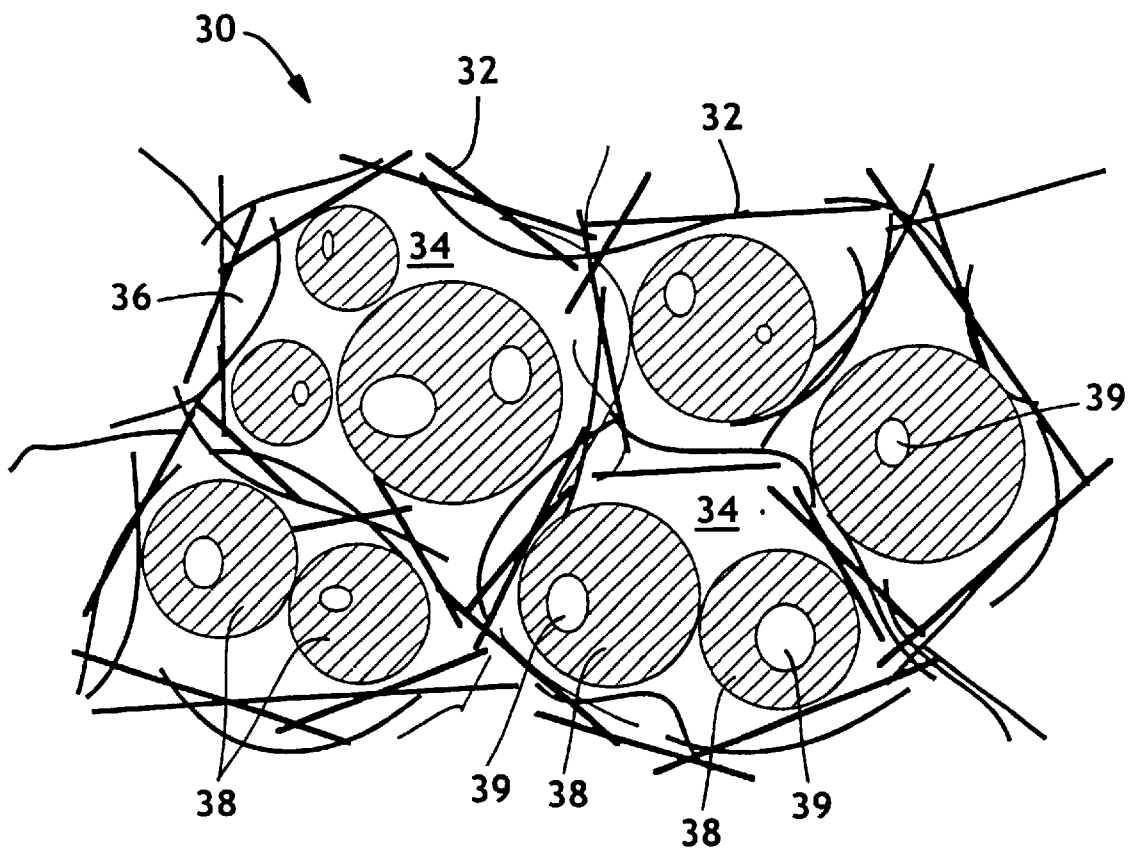
FIG. 4 shows an absorbent fibrous structure wherein foam elements from the structuring composition remain intact occupying the cells defined by the fibers.

FIG. 4 depicts another embodiment based on FIG. 2 in which the foam that served to structure the fibers has not collapsed, but remains partly intact as a structural component of the absorbent fibrous structure 30 occupying a significant portion of the void space 34 in the cells defined by the fibers 32 in fibrous struts. Here are depicted hollow spherical shells 38 of a polymeric foamable material from the structuring composition, the shells having openings 39 such that they are substantially open celled and the void spaces contained therein are in fluid communication with the void spaces defined by the fibrous struts. Single bubbles can occupy cells or multiple bubbles can fill a cell. The occupied spaces as depicted have larger dimensions than the interfiber pore spaces 36, but the foam bubbles can also be smaller. The polymeric foam material 38 preferably is hydrophilic. It can serve as binder material in holding the fibers in place and adhering to the fibers, but additional binder material can also be present between adjacent fibers, as depicted in FIG. 3.

Any bubbles defined by a polymeric foamable binder material or the structuring composition in general during drying or curing of the foam can be larger or smaller than the characteristic fiber length of the hydrophilic fibers. Thus, characteristic dimensions of the residual foam bubbles can be on the order of a fiber length or substantially smaller or greater. For example, if the average diameter of the bubbles is roughly as great or greater than the average length of the fibers, then large open cells are likely to result which offer high void volume, but relatively little capillary pressure for effective wicking. If the bubbles are relatively small, then the resulting structure may be characterized by a plurality of minute cells, preferably open-cells, inside the volumetric regions defined by neighboring fibers. In other words, the fibers, if they could be viewed alone, independently of the binder material, would appear to define open cells or voids substantially larger than the characteristic diameter of the open cells or voids defined by the dry foamable binder material. In this case, the foamable binder material can contribute to capillary pressure beyond what is possible with the fibrous structure alone. In one embodiment, the ratio of foam cell diameter (as measured with respect to the foamable binder material alone) to characteristic fiber diameter is about 1 or less, specifically about 0.3 or less, more specifically about 0.2 or less, still more specifically about 0.1 or less, and most specifically from about 0.01 to about 0.4. In the embodiment where the foamable binder material forms cells smaller than the cells defined by the fibers, the absolute diameter of the cells defined by the foamable binder material can be about 3 mm or less; specifically about 1 mm or less, more specifically about 0.3 mm or less, still more specifically about 0.1 mm or less, and most specifically from about 0.02 mm to about 0.2 mm.

In a preferred embodiment, the structuring composition and/or the foamable binder material of the present invention is substantially hydrophobic when dry or when cured. Preferably, it is not a thermoplastic resin or a molten thermoplastic resin, such that the structuring composition or binder material is substantially free of molten thermoplastic material or, in one embodiment, is substantially free of thermoplastic materials. In one embodiment, the binder material or structuring composition contains less than 10% and preferably less than 2% thermoplastic material by weight. When dried, the binder material should preferably be substantially hydrophilic (e.g., has a pure water contact angle less than 40 degrees and preferably less than 30 degrees).

Figure 5:
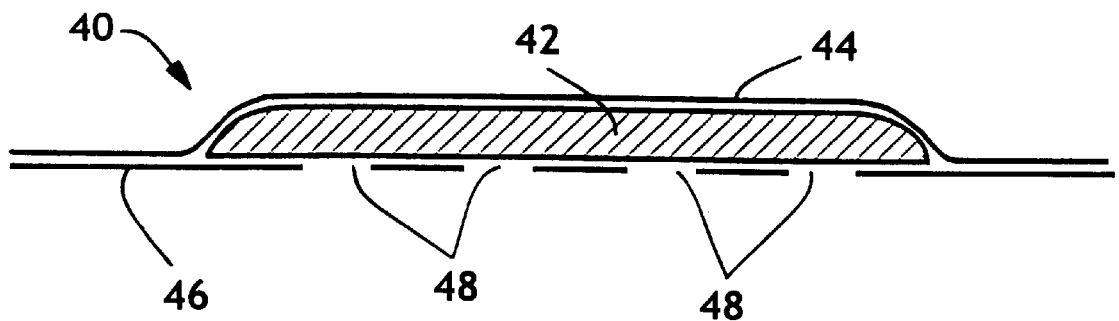
FIG. 5 depicts the cross-section of an absorbent article comprising an absorbent fibrous structure of the present invention.

FIG. 5 depicts the cross-section of an absorbent article 40 comprising an absorbent fibrous structure 42 disposed between a liquid impervious backsheet 44 and a liquid pervious cover 46 intended to be adjacent the body of the wearer. The absorbent fibrous structure can be joined with a layer of fluff pulp (not shown) or other absorbent materials, including layers of creped or uncreped tissue, and specifically molded through-air dried tissue or tissue laminated with superabsorbent material (not shown). The cover has apertures or openings 48 therein, which may also be slits or apertures to provide extensibility when stretched. All components of the article can be stretchable or extensible. The cover 46 can be replaced with a liquid pervious topsheet such as a nonwoven web, including one with elastomeric bonds or laminated to elastomeric materials. The nonwoven web can be combined with additional elements between the topsheet and the absorbent fibrous structure 42. Many other elements (not shown) can be incorporated in such an absorbent article, including a surge layer, an additional absorbent core adjacent the backsheet 44, wings, tabs, flaps, cuffs, elastic bands, odor absorbing materials, and other elements known in the art of absorbent articles and particularly diapers or feminine pads or pantiliners. To render the absorbent article extensible or stretchable, the absorbent fibrous structure is desirably extensible or stretchable. It can comprise elastomeric bonds, with a binder material comprising latex or other known elastomers, and can be joined to elastomeric threads or films or laminated with stretchable material such as a creped tissue.

FIGS. 6 to 12 are photographs and micrographs of embodiments of the present invention, hereafter described in the Examples.

While the principal components of the absorbent fibrous structure of the present invention have been described in the foregoing, such a structure is not limited thereto and can include other components not adversely effecting the desired properties of the absorbent foam. Exemplary materials which could be used as additional components would include, without limitation, pigments, antioxidants, stabilizers, plasticizers, nucleating agents, surfactants, waxes, flow promoters, solid solvents, particulates, and materials added to enhance processability of the absorbent foam. If such additional components are included in an absorbent foam, it is generally desired that such additional components be used in an amount that is beneficially less than about 15 weight percent, more beneficially less than about 5 weight percent, and suitably less than about 1 weight percent, wherein all weight percents are based on the total weight amount of the amount of the polymer, any crosslinking agents, and any other optional components present in the absorbent fibrous structure.

EXAMPLES

Example 1

High bulk foam-stabilized fibrous structures were prepared from dry comminuted papermaking fibers (fluff) with ordinary fresh egg whites serving as a proteinaceous foamable binder material. In a first variant, pure whipped egg whites were prepared and fluff was gradually added. In a second variant, egg whites were mixed with a small quantity of a commercial liquid dishwashing detergent to increase the foaming potential of the mixture, and then fibers were added.

In the first variant, the whites of three refrigerated eggs from a Wisconsin source (Grade A large eggs) were whipped for about 4 minutes with a Sunbeam electric egg beater at high speed in a small cylindrical container about 5 inches in diameter. About half of the egg white froth was removed during the whipping process to maintain adequate volume in the container for the addition of fiber. Small clumps of dry comminuted bleached kraft eucalyptus fiber were dropped into the contained as the egg beater continued stirring the mixture at high speed to effectively disperse the kraft fibers into the foam. Though a balance was not used, an estimated 4 grams of fiber was mixed into the egg white foam over a period of about 3 minutes as whipping continued. The mixture became stiffer with the addition of fibers and increasingly clung to the beater elements rather than residing in the container. The foam-fiber mixture was then removed from the container and scooped onto a metal plate for air drying, with scoops roughly resembling truncated cones having a base radius of about 1 to 2 inches, a height of about 0.5 to 2 inches, and an upper radius of about 0.7 to 1.5 inches. One scoop was dried in a microwave oven, resulting in about 50% or greater loss in height as the mixture dried. Remaining scoops were dried overnight at room temperature, also experiencing substantial collapse during drying. Final drying occurred in a microwave oven for about 12 minutes to drive off remaining moisture. One scoop had an estimated final volume of 15 cc and a room-dry mass of 0.77 g, for a bulk of about 19.5 cc/g. The structure appeared to be predominately fibers and was evidently an open-cell structure, as air would readily pass through the dried scoop under gentle blowing pressure from a human mouth. The dried material felt relatively stiff, being clearly stiffer than an unbonded fluff pulp pad. When wetted, dried scoops of the bulky material retained their shape and displayed obvious hydrophilicity.

It was observed that a scoop of the eucalyptus-egg white mixture which was spread onto a metal plate, with a height of about 0.5 inches, experienced much greater collapse upon drying. Scoops that were loftier, with heights over 1 inch, experienced less collapse upon drying. Without wishing to be limited by theory, it is believed that thicker scoops allowed more fibers to exist in the vertical direction, whereas the spreading motion to put the foam into a thin pad oriented somewhat more of the fibers away from the vertical direction, resulting in less z-direction structural stability during drying.

For the second variant, a small quantity of AJAX® liquid dishwashing detergent with an antimicrobial additive (Colgate-Palmolive), an orange-colored fluid, was added to another batch of 3 fresh, chilled eggs whites as they were whipped to produce a higher void-volume foam with a faint trace of an orange color. Again, about half of the egg white mixture was removed during whipping to leave adequate volume for fiber addition. Roughly equal parts of dry comminuted bleached kraft eucalyptus and bleached kraft southern softwood (CR54 from Coosa Pines, Ala.) were added to the whipped mixture of detergent and about 1.5 egg whites, with addition taking place by dropping small quantities of the fluff into the foam as the egg beater continued whipping the mixture. Approximately 5 grams of fiber were added and dispersed into the proteinaceous foam. The stiff, high-bulk foam was deposited in scoops on a solid surface as before. Some were allowed to dry overnight, another was dried in a microwave after about 2 hours of air drying, and also after about 2 hours of air drying, another scoop was dried in a conventional kitchen oven at about 200° F. for about 15 minutes, followed by drying to completion in a microwave oven.

The hardwood/softwood scoops so prepared exhibited higher bulk and stability than the previous variant with hardwood alone and without detergent. Structures experienced less than about 50% reduction in height during drying, with about 20% height reduction deemed typical. Analysis of a scoop form this second variant indicated that the bulk was about 30 cc/g (the dried sample had a thickness of 1.5 cm, a width of 3 cm, and a length of about 5 cm for a total volume of roughly 23 cc and a room-dry mass of about 0.78 g). The structures readily absorbed water and retained their shape when saturated, though compression could result in permanent void volume loss.

Example 2

A mixture of egg whites, dishwashing detergent, and fluff fibers was prepared as in the second variant of Example 1.

In Run A, 16 g of fresh, room-temperature egg white was mixed with 0.46 g of AJAX liquid dishwashing detergent with an antimicrobial additive (Colgate-Palmolive). The egg white was whipped for about 1 minute with an electric egg beater as in Example 2 in a plastic bowl with an upper diameter of about 8 inches. Eucalyptus fiber was added gradually until 3 grams had been added, but the foam began to collapse after the addition of about 2 grams of fiber. An additional 1.2 g of detergent was added and 10 grams of water followed by whipping, but the high-bulk foam did not return as desired. Without wishing to be bound by theory, it is hypothesized that the egg white foam was not adequately stiff prior to adding the fiber.

In Run B, 1.75 g of the liquid detergent was added to an egg white having a mass of 31 g, which was then beat for several minutes until stiff. At that point, fiberized eucalyptus was then added gradually as beating continued until 2 grams had been added. Then 2 grams of fiberized southern softwood (Coosa Pines CR1654, in fluff form) was added gradually as beating continued. The result was a stable, high-bulk foam. A hex-shaped plastic weighing tray with a volume of about 184 ml was filled with 14.16 g of the wet foam, which was leveled to be flush with the top of the tray. A scoop of 8.8 g of wet foam was placed in a second plate, and 4.7 g of wet foam was placed in a third plate. The air-dry mass of the three portions is 3.49 g, 2.10 g, and 1.06 g, respectively, which includes about 5% moisture still retained by the fibers. The largest portion which filled the hex-shaped tray when wet still substantially filled the tray after air-drying overnight, though an estimated 10–15% shrinkage in height had occurred. Excluding some large voids on the bottom of the hex-shaped foam-fiber portion having an estimated volume of about 10 cc, the estimated macroscopic volume of the fibrous structure is about 155 cc, which gives a macroscopic uncompressed bulk of about 46.7 cc/g (over dry mass basis). At a load of a 0.05 psi exerted by a 3-inch diameter plastic platen mounted to a Mitutoyo thickness gauge, the measured thickness of the sample was 0.754 in and the dry mass of the room dry sample under the platen was about 2.7 g, giving a dry bulk of about 32 cc/g. The sample was then misted with deionized water from a spray bottle to uniformly wet the sample until the wet sample mass was 9.4 (corresponding to a mass of 7.5 g under the confines of the 3-inch platen), which is 280% of the dry sample mass. The bulk of the highly moistened sample was 16.5 cc/g, based on the thickness measured after 20 seconds of residing under the platen at a load of 0.05 psi.

In Run C, a room-temperature egg white having a mass of 30.4 g was beaten with 2 g of the liquid detergent for about 3 minutes to yield a stiff, stable foam. All of a 5 gram portion of comminuted spruce BCTMP pulp was gradually added into the foam as beating continued at medium speed. The high-bulk, stable foam was distributed onto 3 plastic trays. The three portions of the wet foam has masses of, respectively, 11.29 g, 7.89 g, and 6.68 g. One tray was partially dried in a microwave for about 20 seconds, and then all 3 trays were allowed to air dry overnight. Air dried weights, respectively, were 3.14 g, 2.16 g, and 1.82 g. A portion of the dried BCTMP foam was removed from a tray and cut to a substantially rectangular shape having dimensions of about 1.5 cm by 2.3 cm by 3.2 cm for a total volume of about 11.0 cc. The dry mass was 0.24 g, for an uncompressed bulk of about 46 cc/g. A portion of the BCTMP absorbent fibrous structures was later cut having a room-dry mass of 0.8 g and a rectangular cross section of 1.3 in by 2 in with a thickness of 0.65 in as measured by a 3-in platen with a load of 162 g. The load corresponds to 0.05 psi for a 3-in diameter sample, but in this case the applied pressure was about 0.136 psi. The corresponding room-dry bulk was about 32.6 cc/g (accounting for about 5% of the room-dry mass being moisture). The sample was wetted to a mass of 2.0 g by fine spray from a deionized water spray bottle over about a 40 second period. The sample was then placed under the 3-inch platen and the thickness was recorded as 0.335 in after 15 seconds of residing under the pressure of 0.136 psi, indicative of a bulk of about 18.7 cc/g. The bulk would have been even higher at a load of 0.05 psi. Further, had wet strength additives such as Kymene (Hercules Chemical, Wilmington, Del.) or crosslinkers been added, even higher wet bulk values would have been expected, certainly above 20 cc/g.

Figure 6:
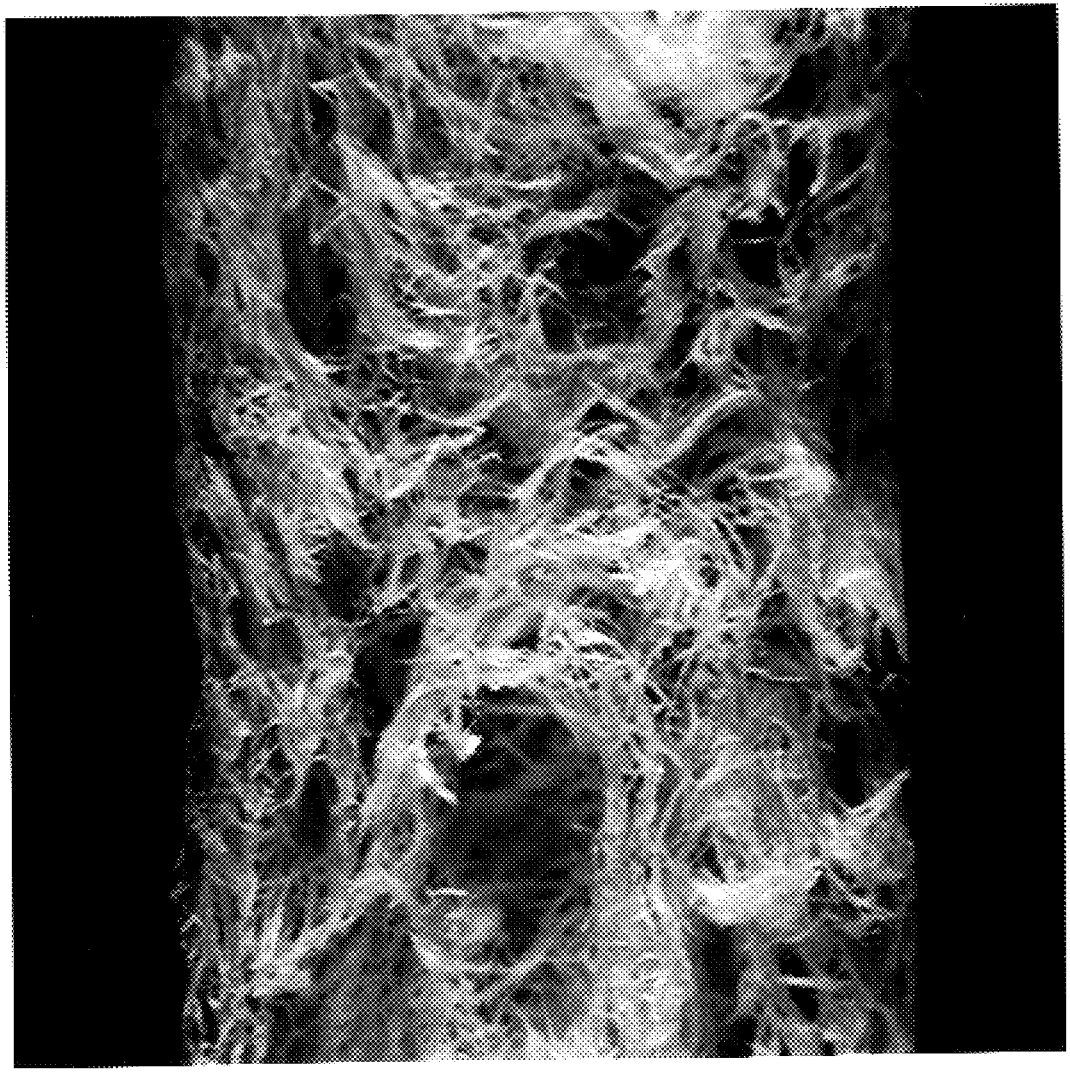
FIGS. 6 to 8 are photographs of an absorbent fibrous structure comprising softwood BCTMP fibers and egg white as a binder material.
Figure 7:
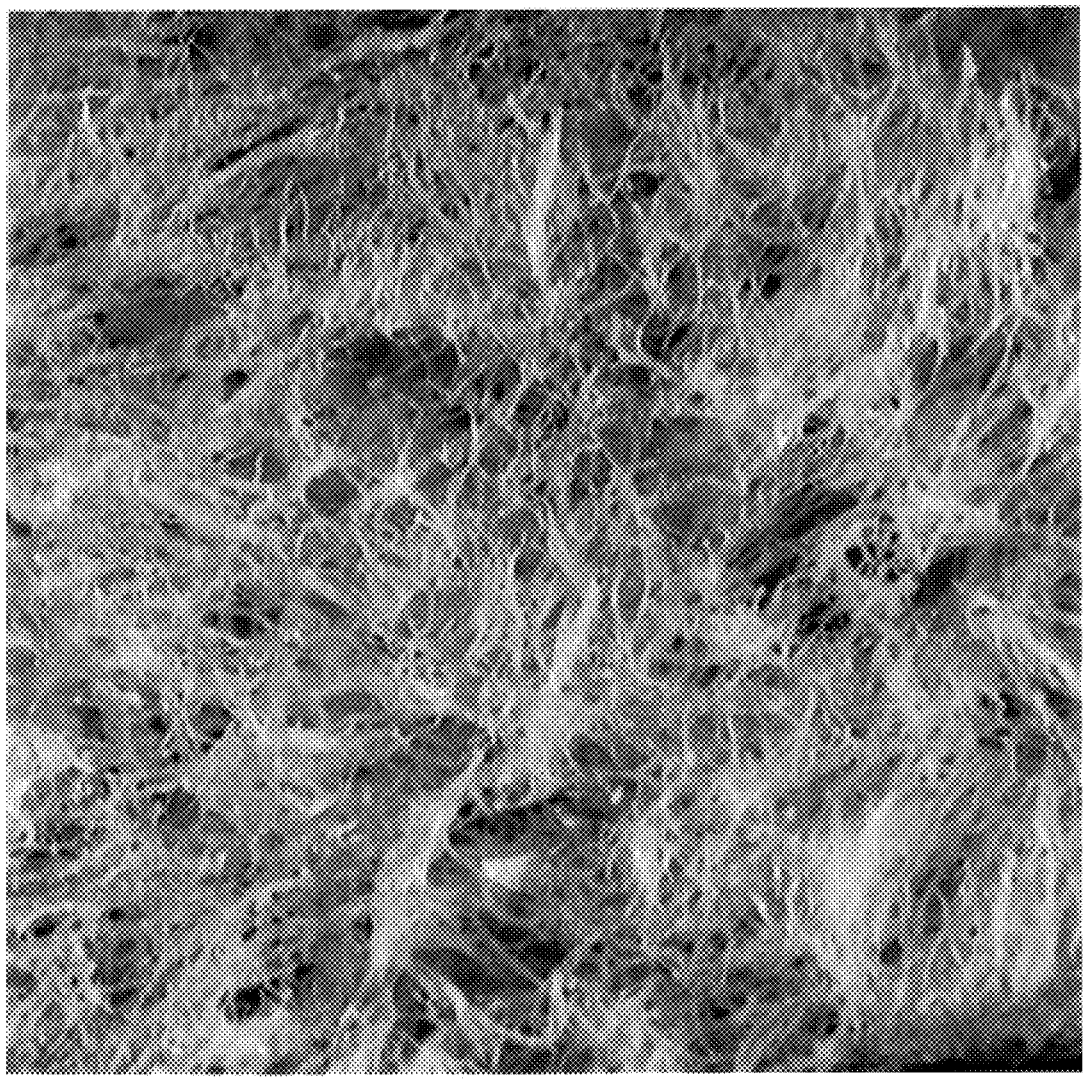
Figure 8:
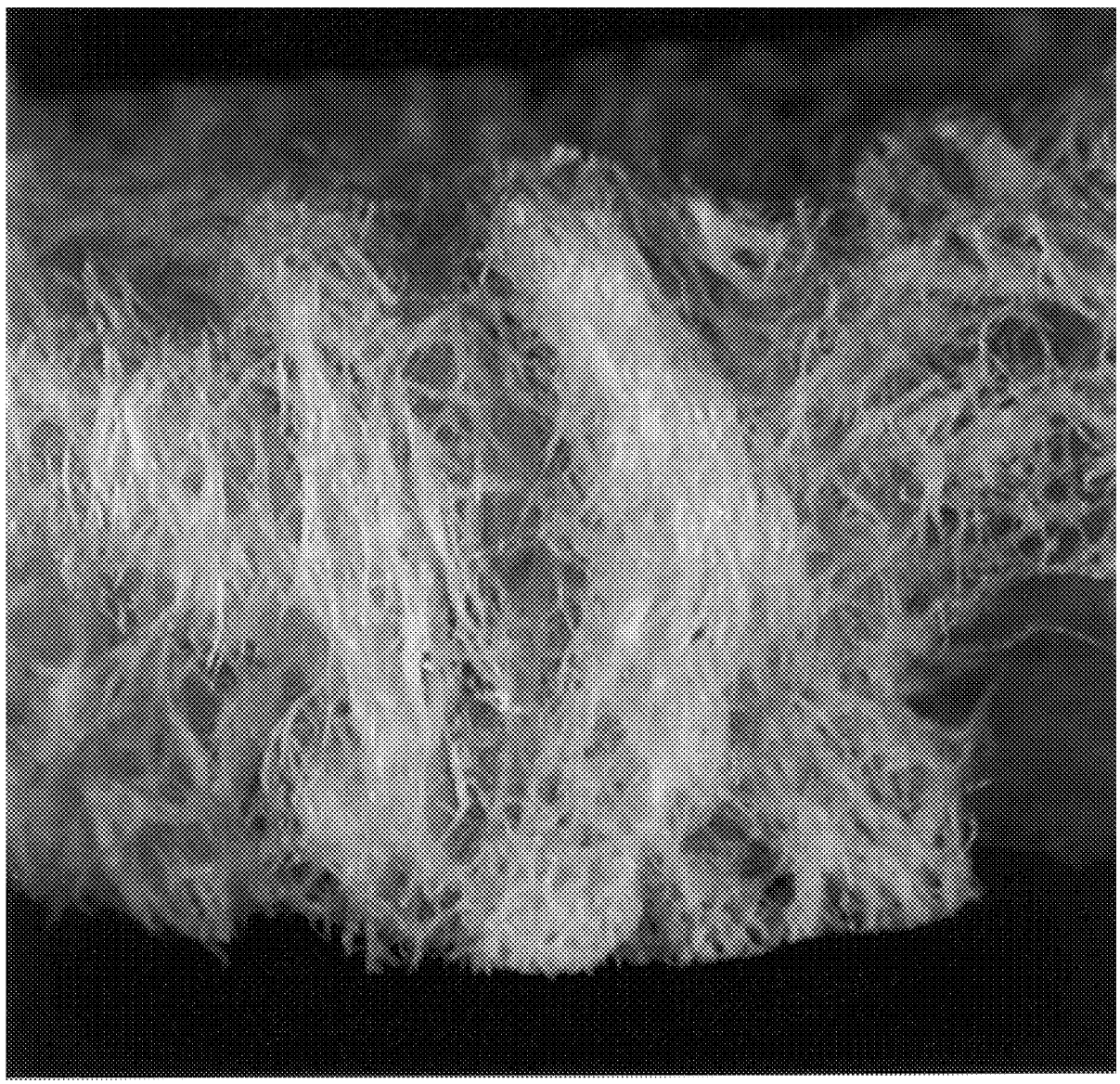

FIGS. 6 to 8 show photographs of small portions of the BCTMP absorbent fibrous structure from Run C. FIG. 6 is a cross section of a sample having a thickness of about 1.3 cm (the distance from the top to the bottom surfaces of the sample in the photograph). A variety of large and small void spaces or cells are evident.

FIG. 7 shows the outer surface of another portion of a sample from Run C. Here, the characteristic cell size is somewhat smaller than the typical fiber length, yet the pore size distribution appears to be bimodal, with a variety of large cells and small void spaces between adjacent fibers.

FIG. 8 shows a cross section from another BCTMP absorbent fibrous structure from Run C above showing fibers that have been substantially oriented in a particular direction, apparently by the flow of the foam, but are substantially heterogeneously distributed.

In most of the samples made with egg white, it was evident that the fibers were not only positioned in space by action of the foam but were oriented by the flow of the foam created by the action of the beating elements. Fibers appeared to be substantially aligned in large regions of the absorbent fibrous structures, with the angle of alignment changing from one location to another, indicative of the flow history of the foam when beating was stopped.

To examine the solids content of the egg white, an egg white having a mass of 29.9 g was dried at 105° C. for about 1.5 hours, being divided into small pieces during drying to increase surface area, and then further dried in a covered container in a microwave until most of the egg white had become discolored rather than white and generally appeared to be crusty and hard. The dried mass was 4.3 g. Thus, in adding about 5 g of fiber to 1 egg white, the resulting structure will be slightly over 50% fiber by mass. Addition of about 4 grams of fiber to an egg white will result in structure having about 50% fiber, and addition of 2 or 3 grams of fiber to an egg white will result in over about 30% and over about 40% fibers by weight, respectively.

Example 3

Carboxymethylcellulose (CMC), an anionic polymer, having a weight average molecular weight greater than 1,000,000 and a degree of substitution of carboxymethyl groups on the anhydroglucose unit of the cellulosic material of about 0.7 was obtained from Aqualon of Wilmington, Del., a subsidiary of Hercules Inc., under the designation CMC-TH carboxymethylcellulose. 20 grams of dry-fiberized eucalyptus fibers purchased from Cinibra, Brazil, with a Canadian Standard Freeness of 625 ml. 1.25 grams of the said CMC were dissolved in 1000 grams of distilled water at a temperature of about 23° C. for 2 hours in a Hobart mixer manufactured by Kitchenaid. The fibers were combined with distilled water and then added to the CMC solution and stirred for another hour. The fiber consistency was about 2%. The slurry was then transferred into a stainless steel pan, wherein the pan had dimensions of 10 inches (width) by 20 inches (length) by 1 inch (depth). The pan was then placed in a freeze dryer, available from The VirTis, Inc., of Gardiner, N.Y., under the designation VirTis Genesis model 25EL freeze dryer. The slurry in the pan was then cooled down to about −25° C. at a cooling rate of 0.04° C./minute in order to freeze the water in the slurry. The slurry in the pan was maintained at about 25° C. for about an hour to ensure substantially complete freezing of the water. The frozen slurry was left in the freeze dryer and then subjected to a vacuum of about 105 millitorrs, provided by a vacuum pump which had a condenser set to a temperature of about −60° C. to about −70° C., for at least about 15 hours. The resultant structures were then treated at 130° C. for 2 hours in order to assist in the crosslinking of the polymers. The resulting fibrous structure has a density of 0.02 grams/cc, with a hand feel and rigidity similar to a fine plastic foam. The CMC superabsorbent foam produced from CMC solution with this method, as reported in the U.S. patent application Ser. No. 08/977,918, "Absorbent Foam," now U.S. Pat. No. 5,985,434 results in an Absorbency Under Load (AUL) at 16.2 grams/gram.

The CMC-eucalyptus absorbent fibrous structure showed good water absorption. The Free Swell Capacity was 21.9 and the AUL was 13.2. To further stabilize the bonds, one section of the material was heated to 180° C. for 10 minutes to promote more extensive crosslinking of the CMC. This sample yielded a Free Swell Capacity value of 25.3 and an AUL of 17.4, showing an apparent improvement in wet properties due to the heat treatment. Another section was sprayed with a Kymene 557-LX solution having 1.1% solids. A section having a dry mass of 1.1 grams was sprayed on both sides with a total of about 10.5 g Kymene solution, while another section with a room dry mass of 6.1 g was sprayed with 30 grams of Kymene solution. The wetted samples did not appear to collapse or swell when wetted, although some collapse occurred during handling from slight mechanical compression. Both of the sprayed samples were then dried in a convective oven at 105° C. for 25 minutes to cure the Kymene and further stabilize the structure. The smaller sample that received the most solution had collapsed significantly during drying and was not tested. The other sample had some regions that were more collapsed, apparently because of higher spray loading. An area near the edge where the spray loading was estimated to be about two-thirds that of the average was tested. The Free Swell Capacity was 22.2 and the AUL was 13.2. The dry mass of the circular disks cut for AUL testing was about 0.08 to 0.1 g per disk. In each case, three disks were tested for both Free Swell Capacity and AUL, with the above reported results being the average of three measurements. The standard deviation for AUL and Free Swell Capacity measurements ranged from 0.5 to 1.5.

Figure 9:
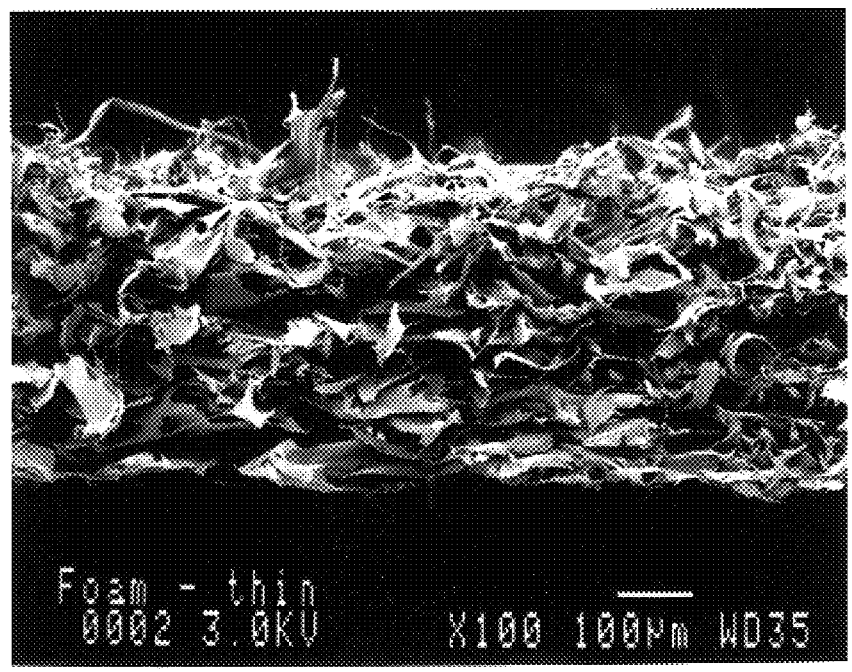
FIGS. 9 to 12 are images taken with scanning electron microscopy of an absorbent fibrous structure made by freeze-drying a mixture of papermaking fibers and CMC.
Figure 10:
Figure 11:
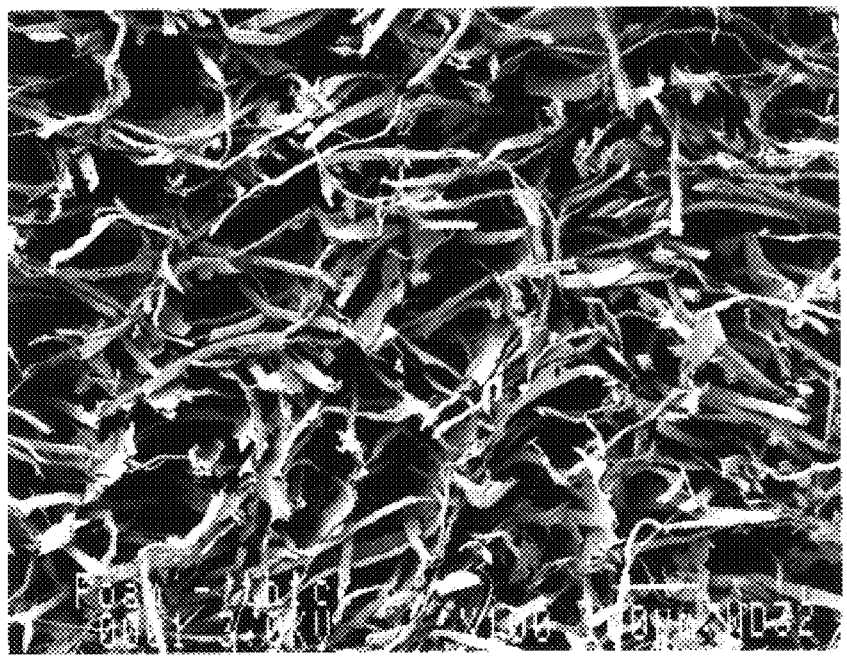
Figure 12:
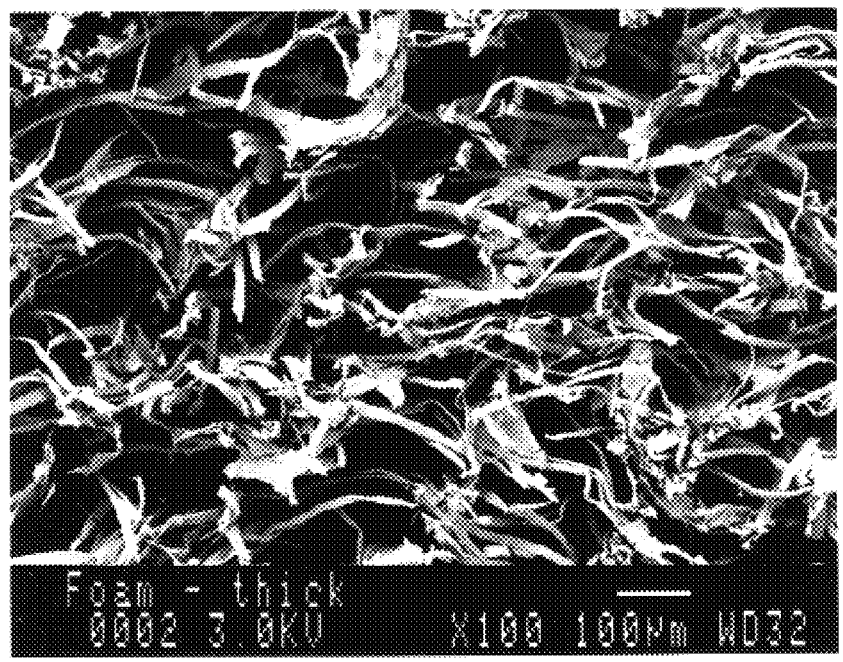

FIGS. 9 to 12 are SEM micrographs of cross-sections of freeze dried foams. FIGS. 9 and 10 show freeze-dried CMC foam without the addition of fibers at magnifications of 100 and 250 times, respectively. FIGS. 11 and 12 show the resulting freeze-dried absorbent fibrous structure from the present example, where the solid phase is about 95% hydrophilic fibers, both at magnifications of 100 times. Cellular void spaces between groups of fibers are evident, with small visible platelets of solid CMC material scattered throughout the assembly. With fibers present, the void volume is substantially greater than in FIGS. 9 and 10, where no fibers have been added.

Example 4

Samples were prepared as in Example 3 above, with the following deviations. Liquid binder material in the form of Kymene 450 (lot #907M15Ky) from Hercules Inc. was used to replace CMC. 10 grams of Kymene solution, having a solids contents of 12.5 wt. %, were added into 1000 grams of distilled water at room temperature in a Hobart mixer. 20 grams of dry fiberized eucalyptus fibers were added into the Kymene solution. Freeze drying conditions were as in Example 3. No heat treatment was used. A high bulk, absorbent fibrous structure was prepared.

Example 5

The binder material was liquid latex, HYCAR 26683 (lot #634-062) from B.F. Goodrich, which replaced the CMC of Example 3. 5 grams of latex liquid, having a solids level of 49.1 wt. %, were added into 100 grams of distilled water at room temperature in a Hobart mixer. 20 grams of dry-fiberized eucalyptus fibers were added into the latex solution. Freeze drying conditions were the same as in Example 3. No heat treatment was used. A soft, highly flexible absorbent fibrous structure resulted, with a cushiony, rubbery feel.

Example 6

As a conceptual example, a high-consistency aqueous slurry of fibers containing chemical binders such as cross-linking agents or adhesives (e.g., latex) can be slurried with an ice or a frozen hydrate representing a removable phase. The fibers so treated become disposed between the frozen phase, which serves to hold the fibers apart and define prospective void volumes between the cells. The removable phase in the slurry can then be removed at least in substantial part by freeze-drying, evaporation, solvent exchange, or the like to leave the fibers in place, which can have incipient bonds formed with the help of the chemical binders, cross-linking agents or adhesives, holding the fibers into a randomized structure with three-dimensional fiber orientation and high void volume. The structure can then be exposed to heat treatment (e.g., 110° C. for 5 minutes) to cure or fully activate said binders, cross-linking agents or adhesives. The resulting pad can have a basis weight of 10–100 gsm or higher and can have a bulk of 25 cc/g. The pad can be embossed to provide channels for flow control, particularly for flow directed along the surface of the pad, and to provide densified zones of high capillary pressure for effective wicking. For example, embossments of elongated sinusoidal lines or an interconnected repeating diamond patterns can be useful in enhancing wicking and controlling flow. Such a pad can serve as an intake material or absorbent core in a feminine pad or diaper, for example.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A method of producing an open low-density absorbent fibrous structure comprising:
   a) combining hydrophilic fibers with a structuring composition to form a mixture, said structuring composition comprising a substantially latex-free binder material and a removable phase;
   b) producing a foam within said mixture; and
   c) binding said fibers together with substantially water-insoluble bonds into a continuous, porous network, wherein said binder material stabilizes the porous network.

2. The method of claim 1, wherein said foam causes physical rearrangement of the fibers in the mixture prior to binding said fibers together.

3. The method of claim 1, further comprising the step of physically rearranging said fibers in at least two dimensions after producing a foam.

4. The method of claim 1, wherein said step of producing a foam occurs during said step of combining the fibers with the structuring composition.

5. The method of claim 1, wherein said step of producing a foam comprises one of generating a fibrous froth with a high-shear mixer, injecting gas into said mixture, adding hollow spheres to said mixture, and depressurizing said mixture.

6. The method of claim 1, further comprising removing a portion of said removable phase.

7. The method of claim 6, wherein said step of removing the removable phase comprises releasing gas from gas bubbles within the mixture.

8. The method of claim 6, wherein said step of removing the removable phase comprises removal of a liquid.

9. The method of claim 6, wherein said step of removing the removable phase comprises one of critical point drying, solvent extraction, supercritical fluid treatment, and sublimation.

10. The method of claim 6, wherein said step of removing the removable phase comprises evaporation.

11. The method of claim 1, wherein said structuring composition comprises a polymer selected from the group consisting of a hydrophilic cellulose derivative, an alginate, a hydrophobic starch derivative, and a gum.

12. The method of claim 1, wherein the mixture has a fiber consistency of 30% or greater and wherein the binder material comprises a protein or a polysaccharide.

13. A method of producing a low-density absorbent fibrous structure comprising:
   a) combining hydrophilic fibers with a structuring composition to form a mixture, said structuring composition comprising a substantially latex-free binder material and a removable phase;
   b) rearranging said fibers in a three-dimensional structure within said mixture;
   c) removing a portion of said removable phase; and
   d) binding said fibers together into a continuous, porous network, wherein said binder material forms bonds between said fibers to stabilize said porous network.

14. The method of claim 13, wherein said bonds formed from said binder material are substantially water-insoluble.

15. The method of claim 13, wherein said structuring composition comprises a blowing agent.

16. The method of claim 13, wherein said removable phase is a liquid.

17. The method of claim 1 or 13, wherein the consistency of the fibers in said mixture is about 4% or higher.

18. The method of claim 1 or 13, wherein the density of said absorbent fibrous structure is about 0.1 g/cc or less.

19. The method of claim 1 or 13, wherein the density of said absorbent fibrous structure is about 0.05 g/cc or less.

20. The method of claim 1 or 13, wherein the removable phase is not removed by sublimation.

21. The method of claim 1 or 13, wherein the absorbent fibrous structure has a dry binder material mass fraction of about 0.6 or lower.

22. The method of claim 1 or 13, wherein the volume of the absorbent fibrous structure is at least 10% greater than the initial volume of the mixture of step (b).

23. The method of claim 1 or 13, wherein said binding step comprises cross-linking said binder material.

24. The method of claim 1 or 13, wherein said binding step comprises curing said binder material.

25. The method of claim 1 or 13, wherein said binding step comprises heating said binder material.

26. The method of claim 1 or 13, wherein said structuring composition further comprises a crosslinking agent.

27. The method of claim 1 or 13, wherein said structuring composition comprises a polysaccharide.

28. The method of claim 1 or 13, wherein said structuring composition comprises a polymer selected from the group consisting of a hydrophilic cellulose derivative, an alginate, a starch, a hydrophobic starch derivative, a superabsorbent polymer, and a gum.

29. The method of claim 1 or 13, wherein said structuring composition contains less than 10% by dry weight of a polysaccharide.

30. The method of claim 1 or 13, wherein said structuring composition comprises a protein.

31. The method of claim 1 or 13, wherein said structuring composition has a bulk viscosity of about 100 centipoise or greater.

32. The method of claim 1 or 13, wherein less than 50% of the mass of said structuring composition is removed from said mixture in non-gaseous form.

33. The method of claim 1 or 13, wherein said structuring composition further comprises a wet strength agent and said method further comprises the step of curing said wet strength agent after the step of adding said fibers to said structuring composition.

34. The method of claim 1 or 13, wherein said structuring composition comprises an High-Internal-Phase-Ratio Emulsions (HIPE) emulsion.

35. The method of claim 1 or 13, wherein said removable phase is a gas.

36. The method of claim 1 or 13, wherein the density of said porous network is about 0.05 g/cc or less.

37. The method of claim 1 or 13, wherein said binder material comprises a polysaccharide or a protein.

38. The method of claim 1 or 13, wherein said structuring composition comprises a surfactant.

39. The method of claim 1 or 13, wherein said structuring composition is substantially free of molten thermoplastic material.

40. The method of claim 1 or 13, wherein said structuring composition is substantially free of thermoplastic material.

41. The method of claim 1 or 13, wherein said binder material is preferentially located at or adjacent to fiber—fiber contact points.

42. The method of claim 1 or 13, wherein said binder material forms an open-cell foam occupying the spaces surrounded by said fibers.

43. The method of claim 1 or 13, wherein the mass of said binder material is less than the mass of said fibers on a dry basis.

44. The method of claim 1 or 13, wherein the mass of said binder material is less than about 20% of the mass of said absorbent fibrous structure.

45. The method of claim 1 or 13, wherein said binder material forms an open-cell foam having a Cell Pore Size of about 500 microns or less.

46. The method of claim 1 or 13, wherein said binder material is hydrophilic.

47. The method of claim 1 or 13, wherein said fibers comprise synthetic fibers.

48. The method of claim 1 or 13, wherein said fibers comprise papermaking fibers.

49. The method of claim 48, wherein said papermaking fibers are substantially unbeaten.

50. The method of claim 48, wherein said papermaking fibers have a Canadian Standard Freeness of about 200 or greater.

51. The method of claim 1 or 13, wherein said fibers comprise about 30% or greater hardwood fibers.

52. The method of claim 1 or 13, wherein said fibers comprise at least 20% high-yield papermaking fibers.

53. The method of claim 6 or 13, wherein said step of binding the fibers occurs in part during said step of removing a portion of the removable phase.

54. The method of claim 6 or 13, wherein said step of binding the fibers occurs in part prior to said step of removing a portion of the removable phase.

55. A method of producing a low-density absorbent fibrous structure comprising:
   a) coating hydrophobic fibers with a hydrophilic fiber coating material;
   b) combining said fibers with a structuring composition comprising a substantially latex-free binder material and a removable phase to form a mixture;
   c) producing a foam within said mixture; and
   d) binding said fibers together into a continuous, porous network, wherein said binder material stabilizes the porous network, and wherein at least about 20% of the surface area of said hydrophobic fibers is coated with hydrophilic material.

56. The method of claim 55, further comprising removing a portion of said removable phase.

57. The method of claim 55, wherein at least about 50% of the surface area of said hydrophobic fibers is coated with hydrophilic material.

58. A method of producing a low-density absorbent fibrous structure comprising:
   a) combining hydrophilic fibers having a consistency greater than 30% with a structuring composition to form a mixture, said structuring composition comprising a non-gaseous phase and a removable phase;
   b) producing a foam within said mixture; and
   c) forming water-insoluble bonds with a binder material to bind said fibers together into a continuous, porous structure.

59. The method of claim 58, wherein said binder material comprises a wet strength resin.

60. The method of claim 58, wherein said structuring composition further comprises a precursor binder material, and wherein said step of forming water-insoluble bonds comprises converting said precursor binder material to a binder material.

61. The method of claim 60, wherein converting said precursor binder material to a binder material comprises one of adding a chemical agent, elevating the temperature of the precursor binder material, and applying radiation.

62. The method of claim 58, wherein a liquid impervious skin forms on a portion of the outer surface of said absorbent fibrous structure.

63. The method of claim 62, further comprising the step of creating openings in said skin.

64. The absorbent fibrous structure made according to any of claims 1, 13, and 58.

65. The absorbent fibrous structure made according to any of claims 1, 13, and 58 having a Wet Bulk of about 10 cc/g or greater.

66. A disposable absorbent article comprising the low-density absorbent fibrous structure made according to any of claims 1, 13, and 58.

67. A method for producing a continuous absorbent fibrous structure comprising:
   a) combining hydrophilic fibers having a consistency greater than 30% with a structuring composition comprising a binder material and a removable phase to form a mixture;
   b) generating a foam within said mixture;
   c) depositing said foam on a moving belt to form a foamed layer without substantial drainage of said structuring composition from said layer; and
   d) curing said foamed layer to form an absorbent fibrous structure.

68. The method of claim 58 or 67, wherein the binder is substantially latex-free.

69. A method for producing a continuous absorbent fibrous structure comprising:
   a) forming an air-laid mat of fiberized hydrophilic fibers on a moving belt to form a fibrous mat;
   b) impregnating said mat with a foamable structuring composition comprising a substantially latex free binder material and a removable phase;
   c) rearranging said fibers in said mat through the action of said structuring composition to create a restructured layer; and
   (d) forming water-insoluble bonds in said restructured layer to form an absorbent fibrous structure.

70. The method of claim 67 or 69 further comprising one of embossing, calendering, or perforating said absorbent fibrous structure.

71. The method of claims 55, 58, 67, or 69, wherein the absorbent fibrous structure has a density of about 0.05 g/cc or less.

72. The method of claims 1, 13, 58, or 67, wherein the hydrophilic fibers are dry.

73. A method of producing an open low-density absorbent fibrous structure comprising:
   a) combining hydrophilic fibers with a structuring composition to form a mixture, said structuring composition comprising a binder material and a removable phase;
   b) producing a foam within said mixture;
   c) removing a portion of said removable phase by one of melting or decomposition of a solid; and
   d) binding said fibers together with substantially water-insoluble bonds into a continuous, porous network, wherein said binder material stabilizes the porous network.

74. A method of producing a low-density absorbent fibrous structure comprising:
   a) combining hydrophilic fibers with a structuring composition to form a mixture, said structuring composition comprising a binder material and a removable phase;

b) rearranging said fibers in a three-dimensional structure within said mixture;

c) removing a portion of said removable phase, wherein said removable phase is a solid; and d) binding said fibers together into a continuous, porous network, wherein said binder material forms bonds between said fibers to stabilize said porous network.

75. A method of producing an open low-density absorbent fibrous structure comprising:

a) combining hydrophilic fibers with a latex-free structuring composition to form a mixture, said structuring composition comprising a binder material and a removable phase;

b) producing a foam within said mixture; and c) binding said fibers together with substantially water-insoluble bonds into a continuous, porous network, wherein said binder material stabilizes the porous network.

76. A method of producing a low-density absorbent fibrous structure comprising:

a) combining hydrophilic fibers with a latex-free structuring composition to form a mixture, said structuring composition comprising a binder material and a removable phase;

b) rearranging said fibers in a three-dimensional structure within said mixture;

c) removing a portion of said removable phase; and d) binding said fibers together into a continuous, porous network, wherein said binder material forms bonds between said fibers to stabilize said porous network.

77. The method of any one of claims 75 to 76, wherein the density of the absorbent fibrous structure is about 0.1 g/cc or less.

78. The method of any one of claims 75 to 76, wherein the density of the absorbent fibrous structure is about 0.05 g/cc or less.

79. A method of producing an open low-density absorbent fibrous structure having a density of about 0.05 g/cc or less comprising:

e) combining hydrophilic fibers with a substantially latex-free structuring composition to form a mixture, said structuring composition comprising a binder material and a removable phase;

f) producing a foam within said mixture; and g) binding said fibers together with substantially water-insoluble bonds into a continuous, porous network, wherein said binder material stabilizes the porous network.

80. The method of any of claims 75, 76 and 79, wherein said structuring composition comprises a polymer selected from the group consisting of a hydrophilic cellulose derivative, an alginate, a starch, a protein, a hydrophobic starch derivative, a superabsorbent polymer, and a gum.

81. The method of claims 1, 13, or 79, wherein the absorbent fibrous structure has a density of about 0.03 g/cc or less.

82. A method of producing an open low-density absorbent fibrous structure comprising:

a) combining hydrophilic fibers with a structuring composition to form a mixture, the hydrophilic fibers having a consistency of either about 4% or less or greater than 30%; said structuring composition comprising a binder material and a removable phase;

b) producing a foam within said mixture; and c) binding said fibers together with substantially water-insoluble bonds into a continuous, porous network, wherein said binder material stabilizes the porous network.

83. The method of claim 82, wherein the hydrophilic fibers are dry.

84. A method for producing a continuous absorbent fibrous structure comprising:

a) combining dry hydrophilic fibers with a structuring composition comprising a binder material and a removable phase to form a mixture;

b) generating a foam within said mixture;

c) depositing said foam on a moving belt to form a foamed layer without substantial drainage of said structuring composition from said layer; and d) curing said foamed layer to form an absorbent fibrous structure.

85. A method of producing an open low-density absorbent fibrous structure comprising:

a) combining hydrophilic fibers with a structuring composition to form a mixture, said structuring composition comprising a substantially latex free binder material and a removable phase;

b) producing a foam within said mixture;

c) binding said fibers together with substantially water-insoluble bonds into a continuous, porous network, wherein said binder material stabilizes the porous network, wherein said step of producing a foam comprises generating a gas by one of a chemical reaction within said mixture and the action of a blowing agent.

86. A method of producing a low-density absorbent fibrous structure comprising:

a) combining hydrophilic fibers having a consistency greater than about 30% with a structuring composition to form a mixture, said structuring composition comprising a binder material and a removable phase comprising a blowing agent;

b) rearranging said fibers in a three-dimensional structure within said mixture;

c) removing a portion of said removable phase; and d) binding said fibers together into a continuous, porous network, wherein said binder material forms bonds between said fibers to stabilize said porous network.

87. A method for producing a continuous absorbent fibrous structure comprising:

(a) forming an air-laid mat of fiberized hydrophilic fibers on a moving belt to form a fibrous mat;

(b) impregnating said mat with a foamable structuring composition comprising a substantially latex free binder material and a removable phase, wherein the impregnated mat prior to forming water insoluble bonds has a consistency of 30% or greater;

(c) rearranging said fibers in said mat through the action of said structuring composition to create a restructured layer; and (d) forming water-insoluble bonds in said restructured layer to form an absorbent fibrous structure.

* * * * *